United States Patent
Edgson et al.

(10) Patent No.: US 6,521,184 B1
(45) Date of Patent: Feb. 18, 2003

(54) APPARATUS FOR MEASURING A DECOMPOSABLE COMPOUND IN SOLUTION

(75) Inventors: Raymond Edgson, Cambridge (GB); Arfon Goodman-Jones, Cambridge (GB); Bo Olde, Lund (SE); Lars-Fride Olsson, Lund (SE)

(73) Assignee: Gambro AB (SE)

( * ) Notice: Subject to any disclaimer, the term of this patent is extended or adjusted under 35 U.S.C. 154(b) by 419 days.

(21) Appl. No.: 09/589,011

(22) Filed: Jun. 7, 2000

Related U.S. Application Data

(62) Division of application No. 08/776,308, filed as application No. PCT/SE95/00888 on Jul. 28, 1995, now Pat. No. 6,114,176.

(30) Foreign Application Priority Data

Jul. 29, 1994 (SE) .............................................. 9402602
Aug. 24, 1994 (SE) .............................................. 9402835
Apr. 10, 1995 (SE) .............................................. 9501315

(51) Int. Cl.[7] .............................................. G01N 27/06
(52) U.S. Cl. .................................. 422/82.02; 436/108
(58) Field of Search ................................ 436/108, 150, 436/174; 435/12; 422/82.02

(56) References Cited

U.S. PATENT DOCUMENTS

| | | | |
|---|---|---|---|
| 3,930,957 A | | 1/1976 | Cummings et al. |
| 4,095,951 A | * | 6/1978 | DiCola et al. ............... 210/180 |
| 4,153,513 A | * | 5/1979 | Edelmann et al. ............. 435/14 |
| 4,311,789 A | | 1/1982 | Nylen et al. |
| 4,465,770 A | * | 8/1984 | Modrovich ............... 252/408.1 |
| 5,132,094 A | * | 7/1992 | Godec et al. ............... 422/68.1 |
| 5,244,811 A | * | 9/1993 | Matthews ..................... 422/80 |
| 5,382,525 A | * | 1/1995 | Spencer ..................... 424/600 |
| 5,672,516 A | * | 9/1997 | Jeffers ......................... 210/758 |
| 5,798,271 A | * | 8/1998 | Godec et al. .................. 422/78 |
| 5,902,751 A | * | 5/1999 | Godec et al. .................. 422/78 |
| 6,114,176 A | * | 9/2000 | Edgson et al. ................ 435/12 |

FOREIGN PATENT DOCUMENTS

| DE | 39 00 119 | 8/1990 |
|---|---|---|
| EP | 0 437 789 | 7/1991 |

OTHER PUBLICATIONS

Patent Abstracts of Japan, vol. 10, No. 9, P–420, abstract of JP., A, 60–165551 (Yokokawa Hokushin Denki K.K.), Aug. 28, 1985.

* cited by examiner

Primary Examiner—Jeffrey Snay
(74) Attorney, Agent, or Firm—Lerner, David, Littenberg, Krumholz & Mentlik, LLP

(57) ABSTRACT

Methods and apparatus for measuring the concentration of decomposable substances, such as urea, are disclosed. The disclosed methods include adding a gaseous buffer, such as $CO_2$, to the solution containing the decomposable compound, measuring the conductivity of the solution, decomposing the decomposable compound, measuring the conductivity of the thus-decomposed compound solution, and calculating the differential conductivities between the two measured solutions. The apparatus for carrying out these methods are also disclosed.

19 Claims, 12 Drawing Sheets

|  | 31a | 31b | 32a | 32b | 33 | 34 | 35 | 36 |
|---|---|---|---|---|---|---|---|---|
| T1 | O | C | O | C | O | O | C | C |
| T2 | O | C | O | C | O | O | O | O |
| T3 | O | O | O | C | O | O | O | O |
| T4 | C | O | O | C | O | O | O | O |
| T5 | C | O | C | C | O | O | O | O |
| T6 | C | O | C | O | O | O | O | O |
| T7 | C | O | C | O | C | C | O | O |
| T8 | C | O | C | O | O | O | O | O |
| T9 | C | O | C | C | O | O | O | O |
| T10 | C | O | O | C | O | O | O | O |
| T11 | O | O | O | C | O | O | O | O |
| T12 | O | C | O | C | O | O | O | O |

APPARATUS FOR MEASURING A DECOMPOSABLE COMPOUND IN SOLUTION

CROSS REFERENCE TO RELATED APPLICATIONS

This application is a divisional of U.S. Ser. No. 07/776,308, filed Apr. 17, 1997, Now U.S. Pat. No. 6,114,176, which was a national stage application of PCT/SE95/00888, filed Jul. 28, 1995.

FIELD OF THE INVENTION

The present invention relates to a method and a device for measuring the concentration of urea or a similar substance in a composite solution. The concentration of urea is difficult to measure directly, and therefore, urea is catalytically decomposed by urease and the differential conductivity is measured.

The solution is preferably a medical solution but can also be a biological solution such as plasma. The present invention relates particularly to the measurement of the concentration of urea in connection with dialysis.

BACKGROUND OF THE INVENTION

The present invention is based on the technique which is disclosed in European Patent No. 0,437,789. This patent discloses, for example, a system for measuring the urea concentration in a complex solution by decomposing urea into ammonium ions catalyzed by urease. It is difficult to measure the urea directly, and it must, therefore, first be converted into ammonium ions. The change in the conductivity due to the contribution of the ammonium ions is measured by means of a conductivity meter.

In German Patent No. 39 00 119 a urea sensor of a similar type is described. A capillary is positioned in a tube, through which blood passes. By means of the capillary, plasma is drawn out of the blood and is allowed to pass through a urease column. The difference in conductivity before and after the urease column is measured and the difference is correlated to the urea content. In order to keep the temperature constant in the measuring apparatus the dialysis fluid is circulated in a closed loop around the urease column and the two conductivity measurement cells.

Japanese Patent No. 60-165551 discloses a similar arrangement, where an ion exchange column is used to remove electrolytes by means of anion-cation-exchange. In this way, the accuracy of the measured values are considerably improved, since the relative change in the conductivity becomes larger due to the fact that the initial conductivity is lower or almost zero. Furthermore, a buffer is added.

U.S. Pat. No. 3,930,957 describes a urea sensor, where an organic buffer solution is added. As an example a solution of 0.05M Tris(hydroxymethyl)aminomethane can be used, which is adjusted to a pH-value of about 6–7 by the addition of glycine.

SUMMARY OF THE INVENTION

In accordance with the present invention, a method and apparatus for measuring the concentration of urea or similar substance in composite solutions is provided. According to the method of the present invention, a method for measuring the concentration of a decomposable compound in a solution has been discovered, comprising adding a buffer in gaseous form to the solution, measuring the conductivity of the solution, decomposing the decomposable compound so as to produce a reacted solution, measuring the conductivity of the reacted solution, and calculating the differential conductivities between the solution and the reacted solution so as to provide a measure of the concentration of the decomposable compound in the solution.

In a preferred embodiment, the buffer in gaseous form comprises carbon dioxide. Preferably, the decomposable compound comprises urea. More preferably, the solution comprises biocarbonate ions. In a preferred embodiment, the decomposing of the decomposable compound comprises catalytically reacting the solution and preferably with urease.

In accordance with one embodiment of the method of the present invention, the adding of the carbon dioxide to the solution comprises diffusing the carbon dioxide through a silicon tube into the solution.

In accordance with another embodiment of the method of the present invention, calculating of the differential conductivities comprises increasing the pressure of the solution in order to increase the solubility of the carbon dioxide in the solution. Preferably, the pressure is increased to about 0.1 MPa.

In accordance with another embodiment of the method of the present invention, calculating of the differential conductivities comprises decreasing the temperature of the solution in order to increase the solubility of the carbon dioxide in the solution. Preferably, the temperature is decreased to about 25° C.

In accordance with another embodiment of the method of the present invention, measuring of the conductivity of the solution and measuring of the conductivity of the reacted solution is carried out by means of a single measurement cell. In a preferred embodiment, the method includes measuring the conductivity of the solution by connecting the single measurement cell at a location upstream of the decomposing step and measuring the conductivity of the reacted solution by connecting the single measurement cell at a location downstream of the decomposing step.

In accordance with another embodiment of the method of the present invention, the method includes measuring the conductivity of the solution by diverting a portion of the solution from the decomposing step.

In accordance with another embodiment of the method of the present invention, the method includes diverting a portion of the solution into a flow path separate from the decomposing step, measuring the conductivity of the solution by means of a first measurement cell in the separate flow path, and measuring the conductivity of the reacted solution by means of a second measurement cell downstream of the decomposing step. In a preferred embodiment, the method includes delaying the flow of the method through the separate flow path whereby the flow of the solution through the separate flow path to the first measurement cell and the flow of the reacted solution to the second measurement cell can take approximately the same amount of time.

In accordance with another embodiment of the method of the present invention, a method is provided for measuring the concentration of a decomposable compound in a solution comprising dividing the solution into a first portion and a second portion, decomposing the decomposable compound in the first portion of the solution so as to provide a first reacted solution, equalizing the temperatures of the first reacted solution and the second portion of the solution in a heat exchanger having a mean temperature, measuring the conductivities of the temperature equalized first reacted solution and second portion of the solution, and calculating the differential conductivity between the first reacted solution and the second portion of the solution, temperature compensating the differential conductivity by means of the mean temperature of a heat exchanger, and calculating the concentration of the decomposable compound from the compensated differential conductivity. Preferably, the decomposable compound comprises urea. In a preferred embodiment, decomposing of the decomposable compound comprising catalytically reacting the decomposable compound in the solution, and preferably catalytically reacting the solution comprises reaction with urease.

In accordance with another embodiment of the method of the present invention, the measuring of the conductivities comprises measuring the conductivity of the temperature equalized first reacted solution and the second portion of the solution with separate conductivity measurement cells.

In accordance with another embodiment of the method of the present invention, the heat exchanger comprises a heat exchange fluid in heat exchange communication with the first reacted solution and the second portion of the solution, and the method includes. providing the mean temperature of the heat exchanger by measuring the temperature of the heat exchange fluid. In a preferred embodiment, the method includes measuring the conductivity of the solution by diverting a portion of the solution from the decomposing step.

In accordance with the apparatus of the present invention, apparatus is provided for measuring the concentration of a decomposable compound in a solution comprising charging means for charging a buffer in gaseous form to the solution, a reactor for decomposing the decomposable compound whereby a reacted solution is formed, and measuring means for measuring the conductivities of the solution and the reacted solution whereby a differential conductivity can be calculated therefrom. In a preferred embodiment, the buffer in gaseous form comprises carbon dioxide. Preferably, the decomposable compound comprises urea, and the solution comprises bicarbonate ions. In another embodiment, the decomposing of the decomposable compound comprises catalytically reacting the solution, preferably reacting the solution with urease.

In accordance with one embodiment of the apparatus of the present invention, the apparatus is a silicon tube in contact with the solution whereby the carbon dioxide can be added to the solution by diffusion through the silicon tube.

In accordance with another embodiment of the apparatus of the present invention, the apparatus includes a bubble detector for detecting bubbles in the reacted solution.

In accordance with another embodiment of the apparatus of the present invention, the apparatus includes pressure increasing means for increasing the pressure of the solution in order to increase the solubility of the carbon dioxide in the solution.

In accordance with another embodiment of the apparatus of the present invention, the apparatus includes temperature decreasing means for decreasing the temperature of the solution in order to increase the solubility of the carbon dioxide in the solution during the measuring step.

In accordance with another embodiment of the apparatus of the present invention, the measuring means for measuring the conductivity of the solution and the reacted solution comprises a single measurement cell.

In accordance with another embodiment of the apparatus of the present invention, the apparatus comprises a first conduit path and a second conduit path, the first conduit path including the reactor, and wherein the measuring means for measuring the conductivities of the solution and the reacted solution comprises a first measuring means for measuring the conductivity of the solution and a second measuring means for measuring the conductivity of the reacted solution, the first measuring means be located in the second conduit path and the second measuring means being located in the first conduit path. In a preferred embodiment, the second conduit path is configured so that the flow of the solution through the first and second conduit paths to the first and second measurement cells takes approximately the same amount of time.

In accordance with another embodiment of the apparatus of the present invention, the heat exchanger is disposed for maintaining the temperatures of the solutions in the first and second conduit paths approximately equal.

An object of the present invention is to provide a method and a device for measuring the concentration of urea in a composite solution by heterogenous catalytic reaction of urea with urease in a reactor column for decomposing thereof, and measuring the differencial conductivity between reacted solution and unreacted solution for providing an indication of the concentration of urea in said solution. According to the invention, carbon dioxide is added to the solution, which comprises hydrogen carbonate ions, before the reaction in the reactor column. The carbon dioxide, together with the hydrogen carbonate ions, form a buffer maintaining the pH-value of the solution within predetermined limits. At the same time, the carbon dioxide contributes to making the relationship between the differential conductivity and the concentration of urea linear over a large range. The addition of carbon dioxide also results in each urea molecule being decomposed into four ions, each contributing to the increase in conductivity.

The carbon dioxide is added in the form of a gas, and preferably in such an amount that the solution is substantially saturated with carbon dioxide. In order to further increase the solubility of carbon dioxide gas in the solution, the pressure of the solution can be raised and/or the temperature of the solution can be lowered. In this way it is assured that a sufficient amount of carbon dioxide is dissolved in the solution for making the relationship linear over as large a range as possible.

The differential conductivity between reacted and unreacted solution can be measured by a single conductivity cell. The unreacted and reacted solutions can be switched to the single conductivity cell in sequence. In this way the two measurements are as equal as possible, independent of the construction of the conductivity cell.

It is also possible to measure the two conductivities with two separate conductivity cells, a first of which is positioned in a first branch including the reactor column and a second of which is positioned in a branch passing the reactor column. Since the measurement of conductivity is highly dependent on temperature, the measurement values must be corrected for temperature or the two different solutions must have the same temperature.

By placing the two conductivity cells in close proximity to each other and passing the two solutions through heat exchanging coils in a heat exchanger, the two solutions attain the same temperature.

Other features, properties and advantages appear from the appended claims.

BRIEF DESCRIPTION OF THE DRAWINGS

The invention will now be described in more detail below with reference to the accompanying drawings in which.

DETAILED DESCRIPTION

Figure 1:
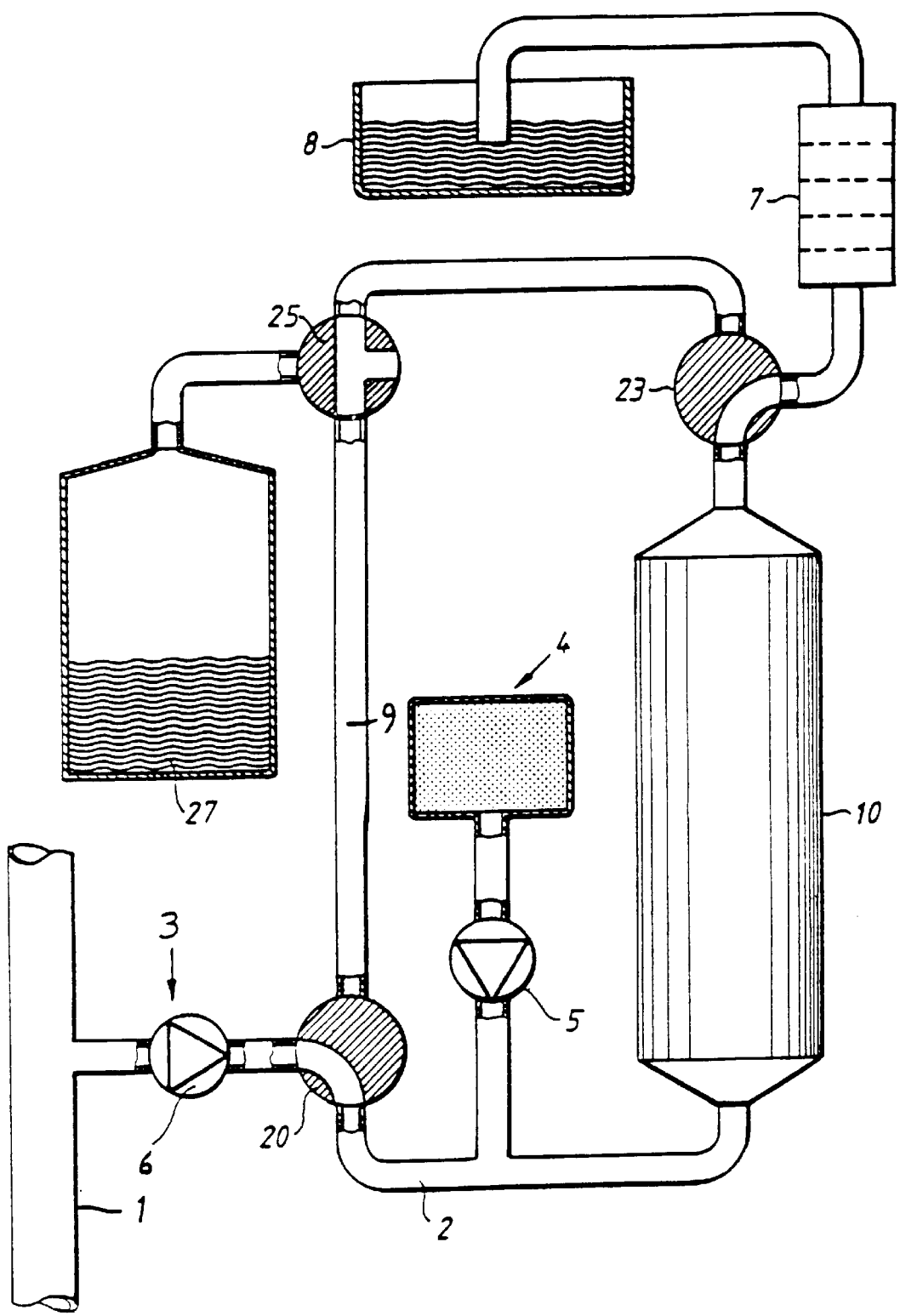
FIG. 1 is an elevational, schematic representation of a urea sensor of the type envisaged by the present invention.

FIG. 1 shows a urea sensor or meter of the type to which the present invention relates.

A fluid or solution on which the measurement is to be carried out passes through a conduit 1. This solution can be a dialysis solution which comes either directly or indirectly from a dialyser.

A sampling device 3 removes a partial quantity of the solution from the conduit 1 and transports this sample to an inlet conduit 2. The sampling device is exemplified in FIG. 1 by a pump 6.

A charging device 4 is connected to the inlet conduit 2 for the addition of one or more substances. The addition is controlled by a pump 5 in FIG. 1.

The sample solution is supplied to a reactor column 10 and is allowed to pass therethrough. The reactor column can contain urease for catalyzing the decomposition of urea into ammonium ions and bicarbonate ions.

The sample is fed from the reactor column 10 to a measuring device 7 which measures the decomposed product in the reactor column. The measurement device 7 can be a differential conductivity cell which measures the change in conductivity before and after the reactor column 10 respectively.

The sample is fed from the measuring device 7 to an outlet arrangement 8.

An ion exchanger can be included in the inlet conduit in order to lower the content of undesirable ions, in order to improve the accuracy of the measuring device.

The invention primarily relates to the measurement of urea, and the reaction in the reactor column is linearised by the addition of carbon dioxide.

The solubility of carbon dioxide is improved by a high pressure and at least the conductivity measurement can take place at increased pressure.

By lowering the temperature, the solubility of carbon dioxide increases, which also can be used with advantage in the present invention.

Solution

The composite solution which is present in conduit 1, and where the content of a substance is to be measured, is a solution of a medical and/or biological type.

In a preferred embodiment, the solution is a dialysis solution, the urea concentration of which is to be determined. A dialysis solution comprises electrolytes with for example $Na^+$, $K^+$, $Ca^{2+}$, $Mg^{2+}$, $Cl^-$, $HCO_3^-$, $CH_3COO^-$ in predetermined concentrations and combinations, as well as possibly further substances such as glycose. When the dialysis solution passes through a dialyser an exchange of low-molecular-weight substances occurs between blood on one side of the membrane of the dialyser and the dialysis solution on the other side of the membrane. Various substances thereby pass from the blood into the dialysis solution, such as urea, creatinine, etc. At the same time certain substances pass from the dialysis solution into the blood, such as bicarbonate ions ($HCO_3^-$).

Other types of solutions to which the present invention can be applied are blood, in which high-molecular-weight substances are preferably first separated, for example by means of a membrane, after which the ultrafiltrate, i.e. blood plasma, is analyzed.

Other types of solutions which can be used according to the present invention are dialysis solutions which are used for peritoneal dialysis, whereby the out-going PD-solution is analyzed.

Additional solutions which can be analyzed are urine, sweat, tear fluid, saliva or other extra-cellular fluids which are sucked out through the skin or withdrawn in another way.

The solution in the conduit 1 can also be a fresh dialysis solution or infusion solution where the concentration of a particular substance is to be determined, for example glycose or penicillin.

The substances of which the concentration is to be measured in the solution are preferably such substances which require catalytic decomposition in order to be measured, and particularly those which require a pH-value lying within a small range, i.e. requiring the presence of a buffer system. Examples of such substances are: urea, L-glutamine, L-citrulline, N-acylaminoacid, penicillin, L-asparagine, cholesterol, and glycose. These substances can be made to decompose or to react during enzymatic influence in the reactor column 10 via known corresponding enzymes. For a more detailed determination of suitable combinations reference is made to European Patent No. 0 437 789 and U.S. Pat. No. 4,311,789.

The invention is described below with reference to urea and urease, but is also applicable to the afore-mentioned substances and other similar substances.

Sampling Devive

A sample is taken from the solution in conduit 1 by means of the sampling device 3. In a preferred embodiment, the sampling device is a pump 6 which is driven so that a constant small flow is taken from the conduit 1. The sample flow can be between about 0.1–10 ml/min, preferably about 0.5–5 ml/min, such as for example 1 ml/min.

The sampling device can also be driven intermittently so that a sample is taken per unit of time, for example at an interval in the region of 5–60 minutes, for example 30 minutes. The volume of the sample can thereby be between about 1–100 ml/sample, preferably about 5–50 ml/sample, such as for example 10 ml/sample.

In one embodiment, the pump is driven in the sampling device 3 so that the sampling flow to. the inlet conduit 2 is proportional to the flow in the solution conduit 1 with a particular proportionality constant. If, for example, the solution in the conduit 1 is a dialysis solution which passes at about 500 ml/min, a five-hundredth part is taken out via the sample device 3, i.e. about 1 ml/min. If the flow in the conduit 1 varies, the flow in the inlet conduit 2 also varies. The advantage with this embodiment is that the present invention can thereby be combined with the invention which is disclosed in European patent application EP 94.102383.0. The pump of the sampling device 3 can also be driven intermittently but each time so that the extracted sample flow is a particular proportion of the solution flow in the conduit 1.

The pump 6 can be a ceramic pump with constant displacement per revolution and can be of the same type which is used in the monitor GAMBRO AK 100. Thus a very accurate metered amount can be taken out from the conduit 1. Alternatively a peristaltic pump of known type can be used, or other similar pumps.

In the case where the content in the conduit 1 consists of blood, the same technique can be used as described in German Patent No. 39 00 119 where a hollow fiber of the same type as used in a hollow fiber dialyser is used for the sampling. The required under-pressure for taking out the ultrafiltrate, i.e. plasma, is created by the pump.

It is also possible to perform the sampling from a container comprising the solution to be analyzed. In this way the container replaces the conduit 1.

Charging Device

The sample which is taken out by means of the sampling device 3 is fed to the inlet conduit 2. An additive may possibly be added in this conduit. In certain cases it is desirable to adjust the pH-value for the solution so that the desired reaction is obtained in the reactor column 10.

In the preferred embodiment the solution which is to be analyzed is a dialysis solution which contains urea and has a pH-value normally of around 7.4. The decomposition of the urea to ammonium ions brings about an increase in that pH-value.

U.S. Pat. No. 3,930,957 describes the addition of an organic buffer in liquid form. An alternative liquid buffer system which can be used is a so-called phosphate buffer consisting of $H_2PO_4^-/HPO_4^{2-}$ which has a pH approximately equal to 7.

One disadvantage with a buffer in liquid form is, however, that it dilutes the solution and adds ions and thus alters the conductivity of the solution before the reaction in the reactor column.

According to a preferred embodiment of the present invention a buffer in gas form is used, namely carbon dioxide ($Co_2$), which cooperates with the bicarbonate buffer already present in the dialysis solution. In this connection carbon dioxide is supplied in gas form from the charging device 4 via the pump 5 to the inlet conduit 2. This is described in more detail below.

The use of carbon dioxide gas as an additive for the dialysis solution comprising bicarbonate and for application to measuring the conductivity gives at least two advantages relative to a buffer in liquid form, namely that the additive of carbon dioxide does not produce any volume change and thus no dilution of the solution, and also that the dissolved carbon dioxide has no inherent conductivity.

By use of a buffer system in connection with a dialysis solution containing urea, in particular carbon dioxide gas, the pH-value can be controlled so that optimal effect is obtained from the urease. At the same time precipitation of calcium carbonate is avoided.

Reactor Column

Figure 7:
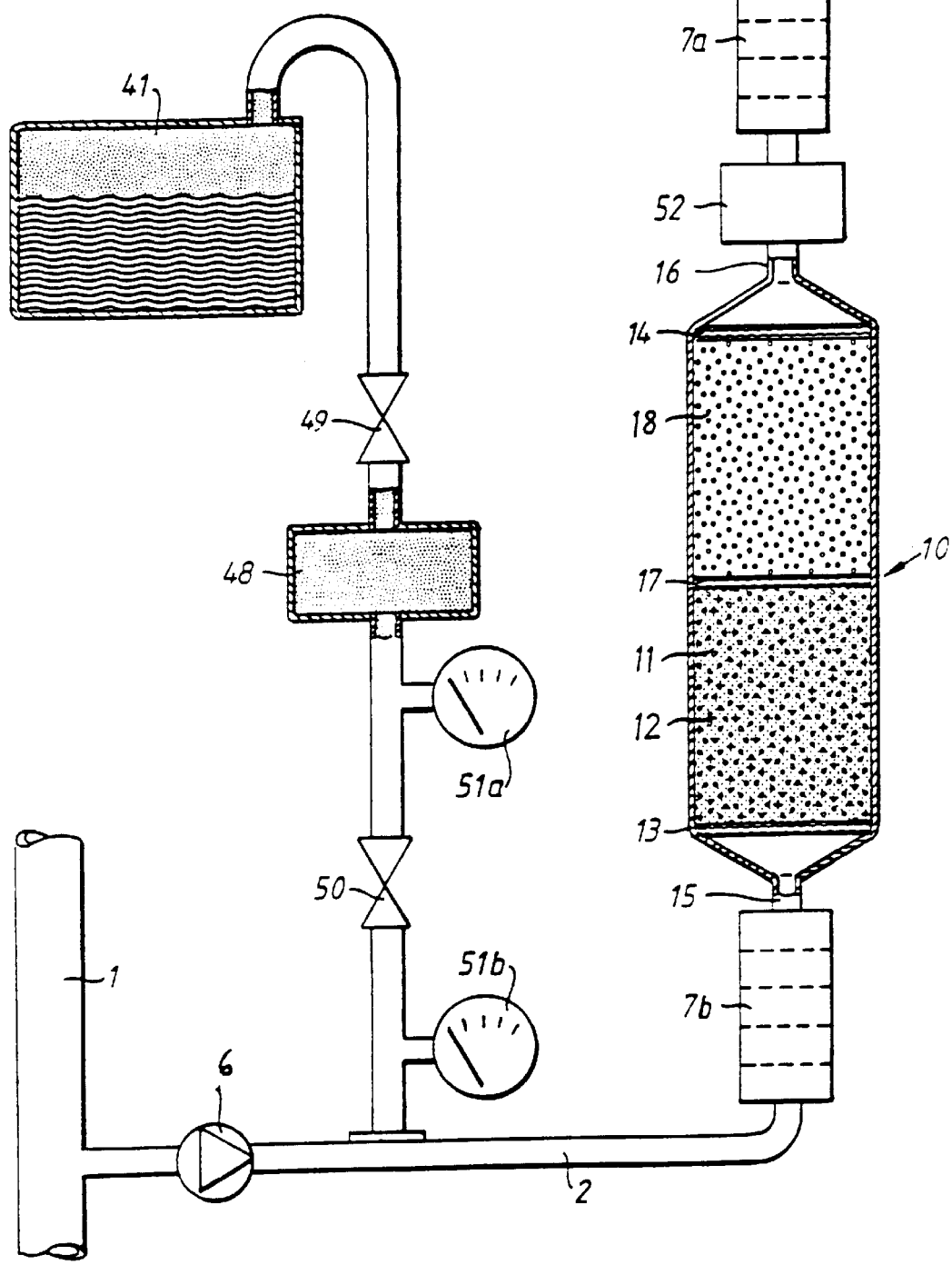
FIG. 7 is a schematic representation of a device similar to the device shown in FIG. 1, showing the use of two conductivity meters.

An embodiment of the reactor column 10 is shown in FIG. 7 and comprises a cylindrical container which contains the enzyme which is required. In a preferred embodiment the column 10 comprises urease 11 which is immobilized by means of aluminium oxide 12 granules. Closely-meshed filters 13 and 14 are arranged at the inlet and the outlet. The filters prevent the urease and aluminium oxide, if released, from passing out of the column 10. The filters furthermore prevent larger particles from entering the column.

The cylindrical container 10 has to have a sufficiently large volume such that the substance which is to be transformed is able to come into contact with, or close to, the corresponding enzyme for the length of time that a decomposition reaction is catalyzed. The column is preferably arranged so that the sample solution comprising the substance reaches the activation proximity of the enzyme to at least 99% for as long as the corresponding reaction is catalyzed.

It is preferred to feed the solution in from below by means of an inlet 15 and to feed out the reacted solution at the upper end of the column by means of an outlet 16. Additionally, a filter 17 is provided which separates an upper part of the column 10, which only contains aluminium oxide 18, i.e. without urease.

It is clear that the column 10 can have various constructions depending on which substance is to be analyzed and which enzyme is used. Thus, the column may also be horizontal or the flow can be reversed and pass from the top downwardly. Additionally, it is possible with intermittent functioning to introduce the sample in the column 10 and to let this remain in the column for as long a time as a reaction is obtained, after which the sample is fed out for analysis and measurement.

In such a preferred embodiment protein and fat are included with the dialysis solution. It is desirable to separate protein and fat before or after the column, whereby one or both of the filters 13 or 14 may constitute a double filter, where one half of the filter has the task of filtering the incoming or outgoing solution and retaining the urease while the other half of the filter constitutes a cellulose filter impregnated with active carbon. In such a filter organic molecules are absorbed, practically speaking, completely. Other filter designs can also be used.

Measuring Device

The measuring device 7 is dependent on the substance which is to be analyzed in the solution. In connection with the preferred embodiment where urea is to be analyzed, the measuring device 7 can be an ammonium ion-sensitive electrode which determines the ammonium ion content in the solution after the reactor column 10. Such a measuring device is disclosed in PCT Application No. WO 94/08641 and U.S. Pat. No. 4,686,479.

The measuring device can also be a pH-meter or a meter for gas which is released, such as ammonia, see PCT Application No. WO 93/22668.

According to a preferred embodiment the measuring device is an arrangement for measuring the difference in conductivity of the solution before and after the urease column 10.

With reference to FIG. 1, the reactor column 10 is preceded by a three-way valve 20, by means of which the inlet flow can be diverted to a shunt conduit 9 and a second three-way valve 23 past the reactor column 10. When the three-way valves 20 and 23 are in the positions opposite as shown in FIG. 1 the dialysis solution passes beyond the column 10 via shunt conduit 9 directly to the measurement cell 7 for measurement of the initial or unreacted conductivity of the dialysis solution, i.e. without decomposing the urea. Then the three-way valves 20 and 23 are switched to their other position shown in FIG. 1 so that the solution can pass through the reactor column 10 and further to the measurement cell 7 and a reaction conductivity value is measured. By this embodiment, the same measurement cell 7 is used for measuring both unreacted and reacted conductivity values, which is beneficial.

Figure 2:
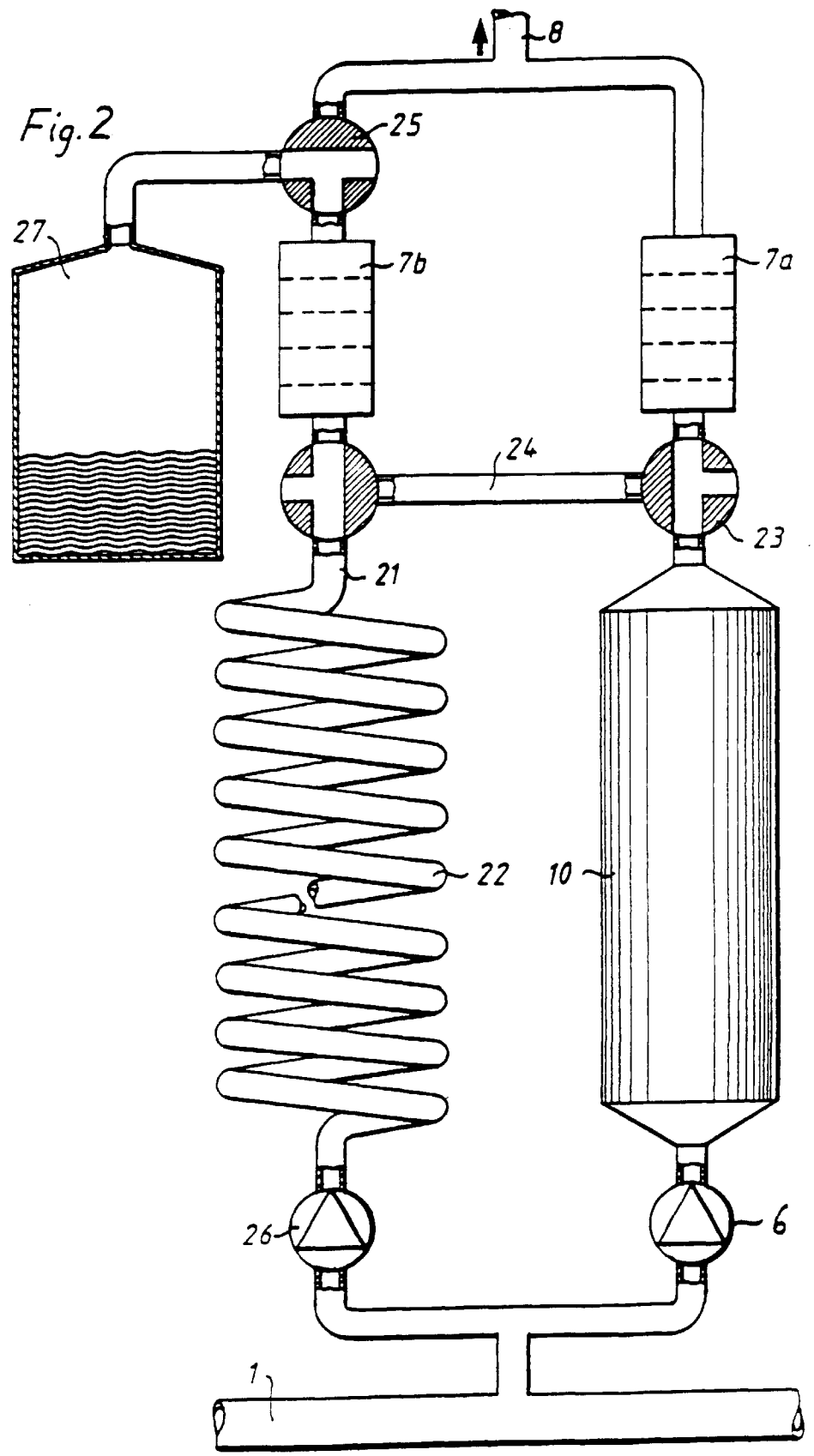
FIG. 2 is a schematic representation similar to FIG. 1, showing the use of two parallel conductivity meters.

In order to carry out the measurement even more reliably it may be suitable to introduce a delay conduit 22 in the shunt conduit 21 with the same volume as the reactor column 10, which is shown in FIG. 2. The delay conduit 22 preferably comprises the same amount of aluminium oxide as the urease-column 10 so that account is taken of the contribution of aluminium oxide to the conductivity. In the embodiment of FIG. 2, two different conductivity cells are used, which however can be calibrated as discussed below.

A further method for determining the conductivity before and after the reactor column is to arrange a measurement cell before and a measurement cell after the column, respectively, which is shown in FIG. 7.

Figure 8:
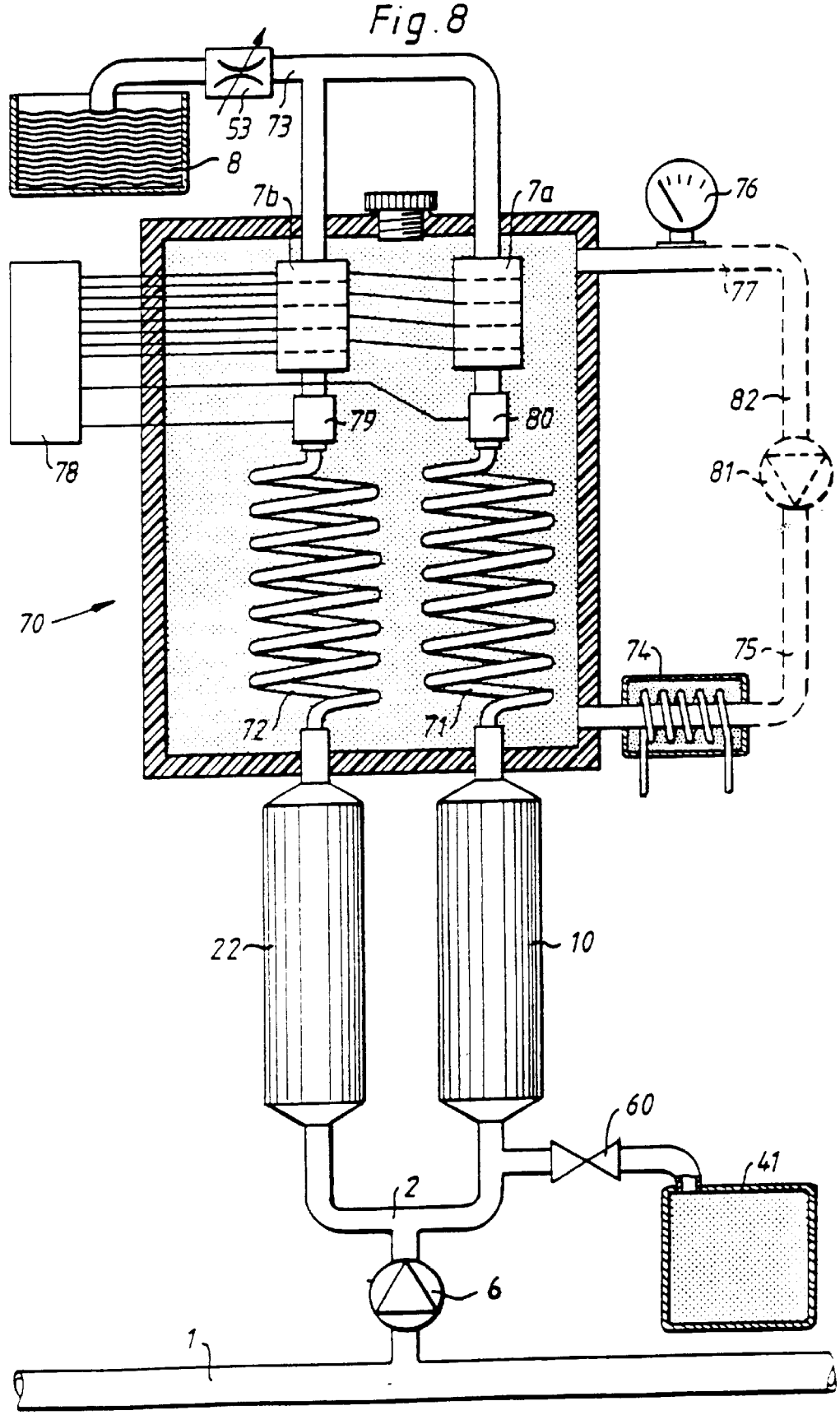
FIG. 8 is a schematic representation of a device similar to the device shown in FIG. 1, showing the use of a heat exchanger.

A preferred measurement method is disclosed in FIG. 8 and involves the sample solution being divided into two parallel flows and measurements being carried out on respective flows with separate measurement cells in order to simultaneously determine the initial conductivity and the reaction conductivity. It will suitably take approximately the same time for the sample solution to reach the respective measurement cell so that the two measurements are carried out on approximately the same sample.

Figures 3, 4:
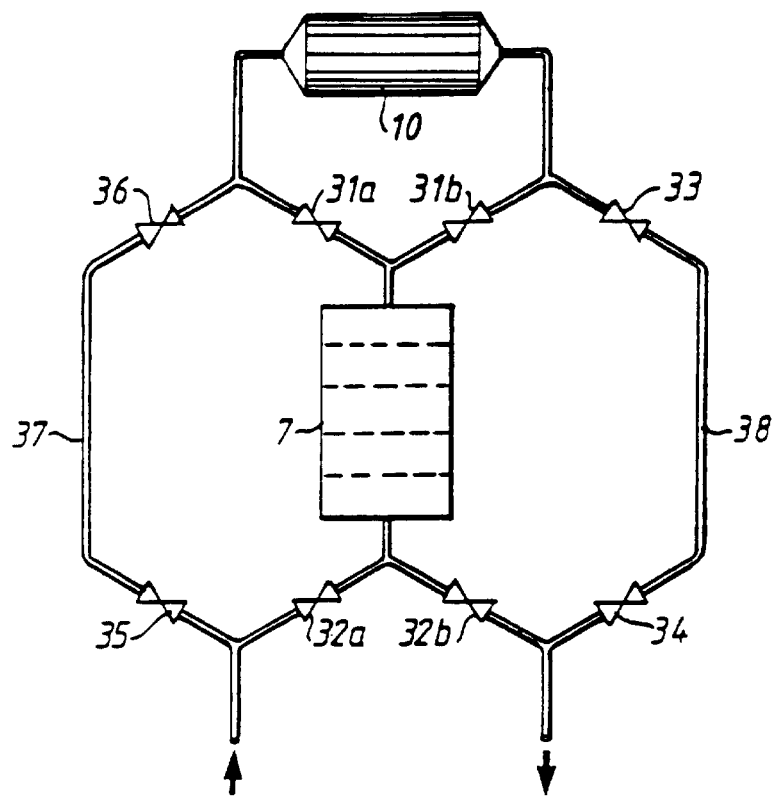
FIG. 3 is a schematic representation showing valves switching one and the same measurement cell before and after the reactor column, respectively.
FIG. 4 is a valve diagram which shows the coupling sequence for the valves according to FIG. 3.

A further way is to use the same measurement cell for measuring the conductivity on the same specific sample not only before but also after the reactor column 10. FIG. 3 shows the reactor column 10 and a measurement cell 7 coupled together with a plurality of valves 31a, 31b, 32a, 32b, 33, 34, 35 and 36. The valves are operated according to the valve scheme in FIG. 4, where O defines open valve and C defines closed valve. The switching scheme has twelve steps denoted T1–T12. After this the same cycle is adopted again.

At time T1 the valves 31a, 32a, 33 and 34 are open and the flow first occurs through the measurement device 7 and thereafter through the reactor column 10. This position is maintained during a relatively long time period so that the reactor column 10 and the conduits are filled with a sample and an initial conductivity is measured.

At time T7 the valves have been switched so that the valves 31b, 32b, 35 and 36 are open. In this position the sample which earlier passed the measurement device 7 into the reactor column 10 flows through the same measurement device 7. Also this position, T7, is maintained during a sufficiently long time so that a reliable measured value of the reaction conductivity can be obtained from the measurement device 7.

In this way the same sample or amount of fluid passes through the measurement device 7 twice (although in different directions) and inbetween has passed the reactor column 10. A particularly accurate measurement can be obtained in this way.

The different switching steps T2–T6 as well as T8–T12 have the task of removing pressure pulses in connection with the switching due to the fact that the measurement device 7 is coupled in parallel with shunt conduits 37, 38 during the switching process. It is of course possible that other valve schemes can be used than that shown in FIG. 4. Similarly the discrete valves 31–36 may be replaced by three-way valves which perform similar functions. It will be clear to a skilled man how such valves should be connected with the guidance provided by FIG. 3 and FIG. 4.

In a preferred embodiment the measurement device 7 is is a conductivity measurement cell which measures the conductivity of the solution which passes the measurement device.

The conductivity measurement cell can be of so-called four-pole type where the electric voltage is supplied to two feed electrodes positioned at a distance from one another. Two detector electrodes are positioned therebetween. The voltage over the detector electrodes is measured and the voltage which is supplied to the feed electrodes is regulated so that the measured voltage is constant. The resultant current is measured and is proportional to the conductivity of the solution. By means of four-pole measurement it is avoided that transition resistances between the supply electrodes and the solution affect the result. The feed voltage is an alternating voltage.

A conductivity measurement cell has a relatively large temperature dependence, for which reason it is necessary to maintain the temperature constant and/or correct for temperature variations as described in more detail below.

For calibration purposes or for taring, a shunt conduit 24 is shown in FIG. 2, said shunt conduit connecting the inlet of the two conductivity cells 7a and 7b with each other. By coupling-in this conduit the conductivity cells can be balanced to give the same measured value. If the conduit 24 is double the conductivity cells can be cross-connected for comparison of the measured values.

Outlet Arrangement

The sample is fed from the measurement device 7 to an outlet arrangement 8, which in FIG. 1 is shown in the form of a collection vessel.

Alternatively, the sample solution can be sent to a drain or be fed back to the conduit 1 downstream of the sampling device 3.

If the present invention is to be combined with the invention according to European Patent Application No. 94.102383.0 as mentioned above, an extra three-way valve 25 is used, said valve being positioned in the shunt conduit 9 (see FIG. 1), or after the conductivity cell 7b in the corresponding conduit in FIG. 2 to the left where the solution has not passed the urease-column. In order to ensure that a certain proportion of the dialysis solution in the conduit 1 passes through the shunt conduit, a separate pump 26 is used (see FIG. 2). The solution is led from the three-way valve 25 to a separate collection bag 27. The volume of solution in the collection bag 27 thus has a predetermined relationship to the amount of solution which has passed through conduit 1, for example 1:500. Furthermore the concentration of the substances included in the collection bag is the same as the average in the conduit 1. By integrating the measured values for the urea sensor over the dialysis time, a total value of the urea is obtained which can be compared with the concentration in the collecting bag (which is analyzed in a different way). In this manner the function of the urea sensor can be monitored and double safety is achieved. Since the urea has been decomposed in the right branch, the solution which has passed along this route cannot be used for this purpose.

Ion Exchanger

In certain cases it is desirable to remove electrolytes from the sample solution before it is fed into the reactor column 10 and the measuring device 7. It is the difference between the conductivity before and after the reactor column 10, which is measured. If the measured value before the reactor column 10 is low or zero, a better accuracy is obtained. For this reason an ion exchanger can be incorporated into the inlet conduit 2 before the reactor column 10, as shown in FIG. 1 with dashed lines at 21.

Such an ion exchanger can be of conventional construction, where the ions are exchanged with corresponding hydrogen ions or hydroxide ions which form water. Such ion exchangers can be very effective but usually require a large amount of space.

Other methods can also be used in order to minimize or eliminate the electrolytes in the solution before the reactor column 10. One example is to use an electrostatic method, where the solution in the inlet conduit 2 is made to pass charged electrode surfaces and where the charged ions are attracted by the electrodes' surfaces whilst the uncharged substances, such as urea, are unaffected.

Additional other known ion exchange techniques can be used.

Urea

The present invention is particularly intended for measuring the urea concentration in a dialysis solution after a dialyser. The urea concentration in this dialysis solution is related to the urea content in the blood which is cleaned by the dialyser.

Urea is often used as an indicator for whether an adequate dialysis has been obtained. Exactly how the urea measurement on the dialysis side is related to the urea concentration in blood and how this is interpreted respectively in order to determine whether the required dialysis has been obtained, is not the subject matter of this invention and will not be described further. There are a large number of literature articles which discuss these questions and attention is directed to European Patent No. 0 547 025 as well as PCT Application No. WO 94/08641.

As concerns measurement of the urea concentration, this cannot be measured directly in an easy manner. As described above the solution which comprises urea must pass a reactor column 10 which comprises urease. Urease is an enzyme which catalyzes the transformation of urea to ammonium ions according to the reaction (1) below:

$$(NH_2)_2 CO + 2 H_2O \xrightarrow{urease} NH_4^+ + NH_3 + HCO_3^- \quad (1)$$

Thus ammonium ions and ammonia are formed as well as hydrogen carbonate ions (bicarbonate). The yield is practically 100% if the contact between the urea and the urease is sufficiently effective.

On the other hand ammonia is decomposed into ammonium ions in dependence on the pH-value of the solution, according to the equilibrium reaction (2) below:

$$NH_3 + H_2O = NH_4^+ + OH^- \quad (2)$$

If the solution comprises a buffer system such as the phosphate buffer mentioned above, this equilibrium (2) will be replaced at sufficiently low pH-value, for example at pH=7, by the following reaction (3):

$$NH_3 + H_2PO_4^- \rightarrow NH_4^+ + HPO_4^{2-} \quad (3)$$

With the aforementioned phosphate buffer the pH-value can be adjusted to approximately 7 and the amount of buffer regulated so that this pH-value is shifted only a very tiny amount. In this way, by suitable choice of the pH-value, practically all the ammonia can be transformed into ammonium ions. Other buffer systems can also be used such as disclosed in U.S. Pat. No. 3,930,957.

The disadvantage with using a buffer of the phosphate buffer type is that it dilutes the solution and contributes to the conductivity before transformation in the reactor column, which makes the measurement of the differential conductivity additionally difficult.. This problem is treated in U.S. Pat. No. 3,930,957 which proposes buffered organic carrier solutions which in themselves have very low electric conductivity and which do not react with the enzyme used.

Carbon Dioxide

In a preferred embodiment according to the present invention it is proposed that a buffer system consisting of carbon dioxide and hydrogen carbonate (bicarbonate) ions be used. Particularly with the measurement of the urea concentration in a dialysis solution, great advantages can be obtained. The dialysis solution normally comprises bicarbonate which together with carbon dioxide forms said buffer system.

Carbon dioxide reacts with ammonia according to the following reaction (4):

$$NH_3 + CO_2 + H_2O \rightarrow NH_4^+ + HCO_3^- \quad (4)$$

The reaction upon which the present invention is based is the sum of reaction (1) and reaction (4), which results in the following reaction (5):

$$(NH_2)_2CO + CO_2 + 3H_2O \rightarrow 2NH_4^+ + 2HCO_3^- \quad (5)$$

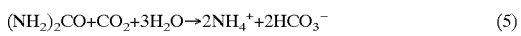

As is clear from the reaction (5) two ammonium ions and two hydrogen carbonate ions are obtained from each urea molecule, all four of which ions contribute to the increase in conductivity. Since carbon dioxide is added in excess, reaction (5) is displaced to the right so that the exchange becomes practically 100%. By addition of surplus carbon dioxide it is further obtained that the pH-value for the solution will be relatively low, which will prevent the precipitation of calcium carbonate.

If the pH-value is under about 7.35, the exchange in the above reaction is larger than about 99.5%. Additionally, the activity of urease is largest within the pH-range of about 6 to about 8. If at the same time the residence time for the solution in the urease column is sufficiently long, a total exchange in excess of 99% is obtained. Thus a pH-value for the solution after the urease-column lying between about 6 and about 8 is preferred, preferably between 6.2 and 7.4.

Figure 5:
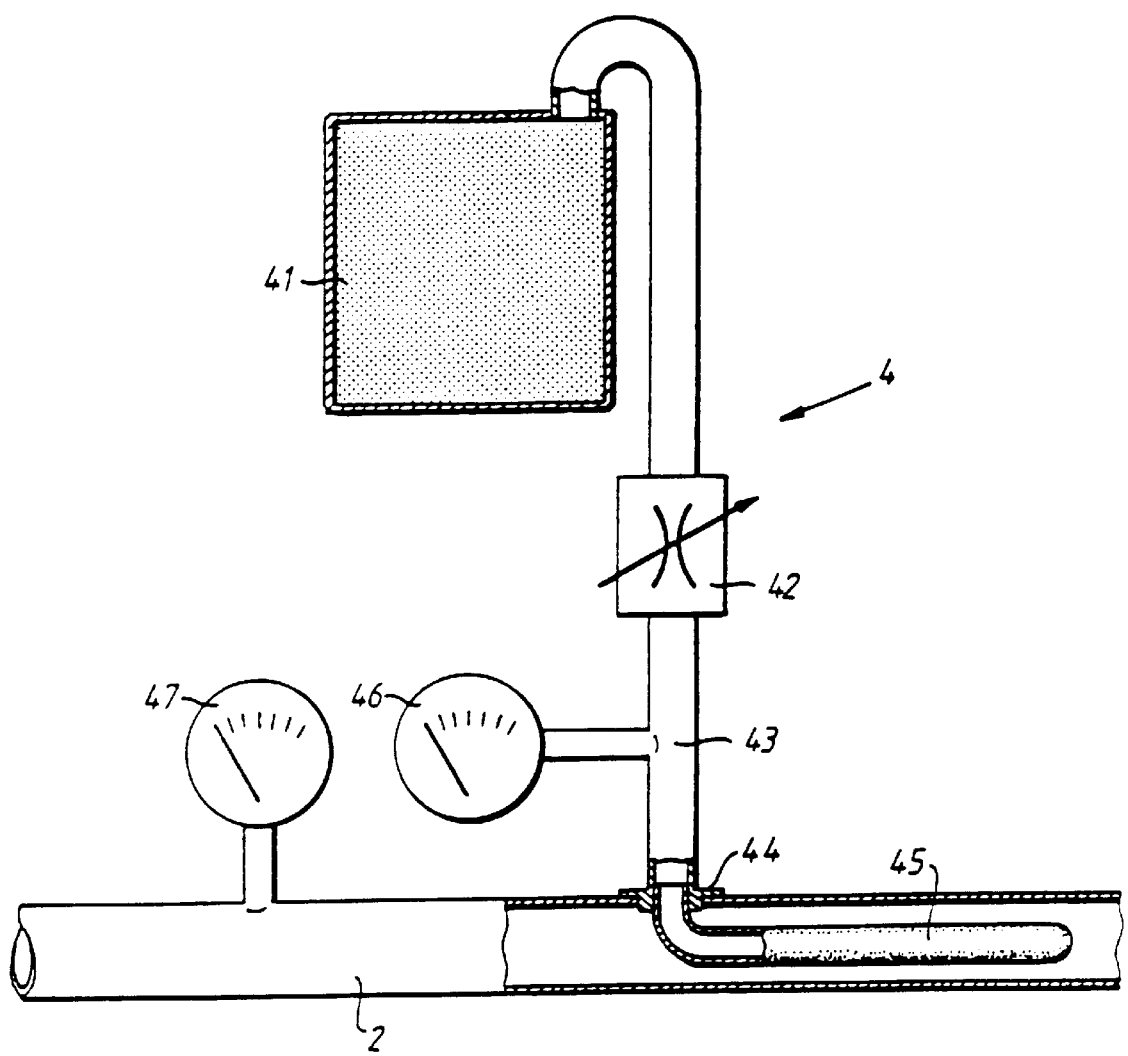
FIG. 5 is a schematic representation of a portion of the device shown in FIG. 1, showing the supply of carbon dioxide gas into a sample conduit.

The carbon dioxide is added by means of the charging device 4. A method for adding carbon dioxide gas to the sample solution in the conduit 2 is shown in more detail in FIG. 5.

The charging device comprises a source of carbon dioxide under pressure 41 as well as a pressure reduction valve 42. Carbon dioxide gas is fed from this source with a predetermined pressure to a conduit 43. The conduit 43 is provided at its lower end with a connector 44 which passes through the wall in the conduit 2 into the sample solution.

A silicon tube 45 or other gas-permeable tube is connected to the coupling 44, said tube being positioned in the conduit 2 substantially concentrically therewith along a predetermined length. The silicon has the property that carbon dioxide gas present within the tube 45 can be diffused through the silicon material and emitted to the solution in the conduit 2.

The regulation of the pressure regulator 42 is is controlled by two pressure meters 46, 47, which detect the pressure difference over the tube 45. These two pressure meters can of course be combined into one differential pressure meter.

The diffusion speed is dependent on the differential pressure across the tube 45. By adapting the length of the tube as well as the pressure difference, the desired amount of carbon dioxide can be fed into the sample solution in the conduit 2. Preferably as much carbon dioxide is added so as to make the sample solution substantially saturated. In this context there is normally a sufficient amount of carbon dioxide which can be used in reaction (5) in order to decompose all the urea to ammonium ions.

At high urea concentrations it is difficult to add a sufficient amount of carbon dioxide gas which will dissolve in the sample solution. In this case a surplus of carbon dioxide gas can be added, said gas being included with the sample solution in the form of micro-bubbles or more or less large bubbles. This gas dissolves partially in the sample solution during transport to the urease column and the remaining amount of carbon dioxide gas is used during the reaction in the urease column.

FIG. 7 shows a further method of supplying carbon dioxide gas to the sample solution in the conduit 2. As in FIG. 5, a source 41 of carbon dioxide gas under pressure is provided. Additionally two valves 49 and 50 are provided, between which a container 48 with predetermined volume is placed. The valve 49 connects the container 48 with the source 41 and the valve 50 connects the container 48 with the conduit 2. Two pressure meters 51a and 51b are arranged across the valve 50.

The function of the charging device according to FIG. 7 is according to the following. The valve 49 is opened and carbon dioxide is fed from the source 41 to the container 48 until the pressure meter 51a detects a predetermined pressure. The valve 49 is then closed and the valve 50 opened, whereby the contents in container 48 is supplied to conduit 2.

When the pressure meter 51a or 51b detects a low pressure, the valve 50 is closed and the valve 49 is opened for a renewed filling of container 48.

Since the volume of the container 48 and the pressure difference are known, the supplied amount of carbon dioxide in the conduit 2 can be determined.

The valve 50, in the open condition, can perform a certain throttling so that supply of carbon dioxide gas occurs with a relatively even speed. By regulating the degree of throttling in the valve 50 during its open time, the amount of gas supplied per unit of time can be regulated.

It is also possible to operate the valve 50 so that a large bubble of carbon dioxide gas is fed into the sample conduit 2 so that the bubble fills up the complete cross-section of the conduit 2. During the following transport towards the reactor column, the bubble of carbon dioxide gas dissolves partially in the sample solution next to it so that this becomes substantially saturated with carbon dioxide. The remaining amount of carbon dioxide gas is finally dispersed by the filter 13 in the reactor column 10 (see FIG. 2) so that the carbon dioxide gas is evenly distributed in the sample solution. The inlet conduit 15 should thereby be conically shaped so that the sample solution is divided over the whole cross-section of the reactor column 10. During passage through the reactor column 10, the carbon dioxide is used in reaction (5), whereby the surplus of carbon dioxide is used up.

In order to ensure that no carbon dioxide in gas form remains in the solution which leaves the reactor column 10, which would disturb the following conductivity measurements, the outlet conduit 16 (see FIG. 7) may be provided with a bubble detector 52, for example an ultrasound detector. The output signal from one such bubble detector can be used in many ways. It can be used to indicate feasibly erroneous measurement values and/or to regulate the supply of carbon dioxide gas. In the latter case it should be observed that the time delay from supply to detection is relatively long, for example four minutes. If the concentration of urea does not change too quickly, an efficient and optimal regulation caN however be obtained.

In connection with the bubble detector 52 a gas separator 62 (see FIG. 6) may be present, separating any possible gas in free form from the solution in outlet 16.

The carbon dioxide gas source 41 is preferably formed by a pressure container with carbon dioxide gas in condensed form, which immediately vaporizes upon release and corresponding reduction of pressure. Such carbon dioxide cartridges are available in different sizes. The consumption of carbon dioxide gas is ever so small that such a carbon dioxide cartridge of small dimension will suffice for very long periods of operation.

An alternative source of carbon dioxide gas can be the production of carbon dioxide gas in-situ. One way is to heat sodium bicarbonate powder ($NaHCO_3$) to a high temperature, for example over 50° C. In this way the sodium bicarbonate is decomposed and carbon dioxide gas is given off. The bicarbonate can be provided in a small container which is placed on a heating element. When the apparatus is to be used, the heating source is activated and the carbon dioxide gas is given off after a short time. The cartridge is of course replaceable. Other methods are known in the art. The exact method of manufacturing carbon dioxide gas does not form part of the subject matter of the present invention, but reference is made to European Patent No. 0 481 257 where a method for production of carbon dioxide gas is described.

During the reaction in the urease column 10 the pH-value of the solution rises, particularly if the urea concentration is high and the content of carbon dioxide gas is too low. If the pH-value rises above about 7.4 there is a risk for precipitation of calcium carbonate and magnesium carbonate (calcium ions and magnesium ions are normally part of the dialysis solution). If such precipitation occurs in the measurement cell 7, this can very soon lead to erroneous measured values and the measurement device must be cleaned.

In order to obtain a sufficiently low pH-value in the solution which passes the measurement cell 7, it can be desirable to add carbon dioxide gas also at the outlet from the urease-column 10, i.e. at the outlet 16.

It is also possible to provide the column 10 with a second inlet for carbon dioxide approximately at the filter 17 (see FIG. 7) or in other places, whereby it is ensured that the pH-value is always sufficiently low to avoid precipitation of calcium carbonate in the conductivity measurement cell.

Preferred pH-values (at a position after or inside the conductivity cell) are between 5.5 and 8.5, preferably between 6 and 8. With use of carbon dioxide and bicarbonate as the buffer, it is preferred that the pH-value lies between about 6.2 and about 7.7, preferably between 6.3 and 7.4.

Pressure

It is known that the solubility of carbon dioxide gas in water is essentially proportional to the pressure in the water. This fact is used in the embodiment shown in FIG. 7.

An adjustable throttle valve 53 is arranged after the outlet 16 of the urease column. The throttle valve 53 functions together with the pump 6 in order to raise the pressure in the conduit 2 and the urease column as well as the measurement device 7a if bubbles are detected by the bubble detector 52.

The carbon dioxide gas then dissolves due to the increase solubility. The pressure is suitably re-adjusted to normal pressure as soon as the supply of carbon dioxide has been reduced so that no bubbles remain.

In another embodiment the throttle valve 53 is used together with the measurement device 7a in order to detect the occurrence of bubbles in the sample solution which upsets the measurement in the measurement device 7a, like a replacement for, or complement to, the bubble detector 52. At predetermined intervals, where it is desirable to check whether the measured results are reliable, the pressure is raised momentarily by activating the throttle valve 53. The pressure increase can be monitored by the pressure meter 51b or a separate pressure meter. If the pressure rise results in a change in the measured value in the measurement device 7a, this is a sign that the sample solution contains gas bubbles which disturb the measuring. This information can be used in order to reduce the supply of carbon dioxide gas, after which a new test is carried out after a certain time in order to verify that the change has given the desired effect.

The pressure meter 51b can also be used in order to ensure that the sample solution 2 is always at approximately the same pressure, for example atmospheric pressure. If the sampling occurs at the outlet from a dialysis machine, the pressure before the pump 6 can vary considerably. If the discharging device 8 is formed by a return conduit to conduit 1, the whole of the sample conduit 2 will be at that pressure which is present in the conduit 1. By manoeuvring the throttle valve 53 and the pump 6, which is monitored by means of the pressure meter 51b, the desired pressure in the sample conduit 2 as well as the measuring device 7a can be set, for example at somewhat above atmospheric pressure.

The aforementioned pressure increase only effects the measured result in the measurement device 7a to a very small extent in normal cases if the measurement device 7a is a conductivity cell. With the use of other types of measurement devices, one has to correct for the pressure-dependence of these measurement devices when applying the aforementioned method with pressure increase.

As an alternative to the method described above a local pressure increase in only the measurement device 7a can be used. For this an extra pump arranged before the measurement device 7a and a throttle valve arranged after the measurement device 7a are used. The extra pump and throttle device 53 are controlled so that the pressure in the reactor column 10 is not affected. Apart from this the function is the same as described above.

It is also possible to use a permanent pressure increased. The pressure increase could be in the range 0.03–0.3 MPa, preferably about 0.1 MPa. In this way a sufficient amount of carbon dioxide gas can dissolve in the solution in order to satisfy the reaction (5) and at the same time to ensure an outlet pH-value below about 7.4 up to a urea concentration of about 35 mM, without extra addition of carbon dioxide gas.

Temperature

It is known that the logarithm of the solubility of carbon dioxide gas in the sample solution in the conduit 2 is inversely proportional to the temperature. Normally the temperature of the used dialysis solution is about 36–37° C.

In order to avoid dependence on the temperature in the incoming dialysis fluid, the sample solution can be heated up, by means of a heating element, to a fixed temperature which lies at a value between about 38 and about 45° C., preferably about 40°. The reason that: the temperature is chosen to be so high is that it is higher than all expected incoming temperatures, for which reason no cooling is required and consistent measurements are obtained independent of the incoming temperature.

It is desirable to maintain the temperature substantially constant during the passage of the sample solution through the device, i.e. from the sampling device 3 through the reactor column 10 and the measurement device 7. At least the temperature of the reactor column should be constant in order to obtain uniform activity. However the temperature should not be raised (at least not too much) before the conductivity measurement cell in order to avoid possible bubble formation due to surplus carbon dioxide.

According to one embodiment of the present invention the temperature is instead lowered on the incoming sample solution by means of cooling. Such cooling can occur in many different ways, but since the amount of solution which is to be cooled is relatively small, Peltier-elements can be used where the electric current is directly converted into cooling. The sample solution is made to pass a Peltier-element 55 and current is supplied so that the required temperature drop is obtained as shown with dashed lines in FIG. 6, which is detected by a temperature sensor 56 positioned downstream of the Peltier-element 55. A suitable temperature in this alternative embodiment is about 25° C.

The temperatures used should lie in the range of about 20° C. to about 50° C. The reason for this is that below about 20° C. the urease-enzyme has low effectiveness, which means that the transformation from urea to ammonium ions takes too long time. Above about 50° C. the urease-enzyme is decomposed, which of course is undesirable. A temperature between about 25° C. and about 45° C. is therefore preferred.

By using lowering of temperature with Peltier-elements, it is ensured that a sufficient amount of carbon dioxide gas can always dissolve in the sample solution in the conduit 2.

A lowering of the temperature in connection with the measurement cell can be used in order to detect the presence of carbon dioxide gas which upsets the measuring, analogous with the aforementioned pressure increase. With lowering of the temperature in the measurement cell the solubility of carbon dioxide increases and carbon dioxide gas in bubble form will possibly dissolve. In order to compare conductivity values before and after such a temperature reduction, temperature compensation of the measured values is however required which can be difficult to achieve with desired accuracy.

Figure 6:
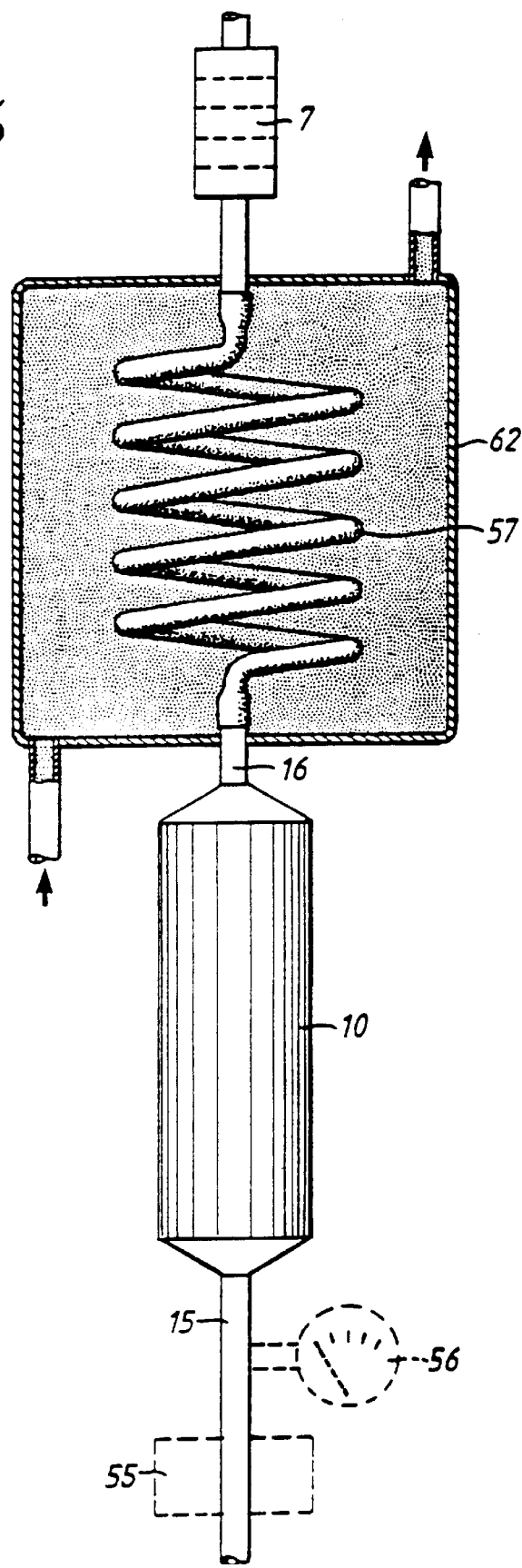
FIG. 6 is a schematic representation of a portion of the device shown in FIG. 1, showing an alternative method of eliminating bubbles of carbon dioxide gas.

FIG. 6 shows a gas trap 62 in the form of a gas-permeable tube 57 of silicon. Outside the tube there is a solution with a low content of carbon dioxide, for example dialysis solution, such as the content in the heat exchanger as described in connection with the preferred embodiment in FIG. 8 (see below). The surplus of carbon dioxide gas inside the tube 57 may possibly be given off to the fluid outside the tube 57, particularly if a pressure difference is present. Other types of gas separators can also be used.

Priming

The urease-column 10 contains a dry powder which has to be moistened before use. This can take place by allowing a physiological sodium chloride solution to pass through the urease-column and the measurement device 7.

Alternatively one can use the dialysis solution which is used by the dialysis machine during its start-up period in order to moisten the urease column and put this into an operation-suitable condition. The dialysis machine carries out a start-up procedure called "priming", whereby the dialysis solution is circulated through the dialysis machine's system without the dialyser which is shunted. This solution can also be used for priming the urea-sensor.

Disinfection

Normally no particular cleaning of the urea-sensor is required. It is however recommended to flush out the urea-sensor after completed use, for example by allowing a physiological sodium chloride solution to pass through the urea-sensor for a predetermined time. A disinfection with raised temperature is normally not required. However the disinfection of the dialysis monitor and the urea sensor can be coordinated so that the disinfection solution may also pass through the urea sensor. In this case a heat disinfection is preferred, but also disinfection using citric acid etc. may be used (CleanCart).

In certain cases the dialysis solution contains glycose which can cause problems. By flushing after use such problems are however avoided.

The urea sensor according to the invention can be used completely separate from a dialysis monitor. In this case the urea sensor is connected to the outlet tube of the monitor. Of course the urea-sensor can be fixed to the casing of the apparatus and connected at a different location, for example immediately after the dialyser. It is also possible to completely integrate the urea sensor into the dialysis machine and/or provide the urea sensor with an electronic interface to the dialysis machine.

Quality Test

Before using the urea sensor it is preferable to establish that everything is working satisfactorily. To this end, a small amount of solution containing urea at a particular known concentration is supplied to the conduit 2 and may pass the urea sensor. If the measurement device 7 does not produce an expected measured value it has to be exchanged and sent for repair/service.

Such a quality control can be carried out in a relatively simple way in that the urease column 10 comprises a small amount of urea in powder form at its inlet 15. As soon as the physiological sodium chloride solution or other solution is supplied for priming, the urea powder is dissolved and transformed by the urease column 10 into ammonium ions which give a reading on the measurement device 7. In this way only one exchangeable and disposable unit is required, namely the urease column 10 containing said urea powder.

The urease column 10 consists of a cartridge which is exchangeable. Before a dialysis treatment a new cartridge is put into place and priming occurs as described above.

With the case of manufacturing carbon dioxide gas in-situ, a second cartridge containing the necessary ingredients can be used. These two cartridges can form a unit by being built together in a suitable manner. The unit is exchanged in connection with each measurement and is dimensioned to allow measuring during a normal dialysis treatment, which can be about four hours with haemodialysis.

Preferred Embodiment

FIG. 8 shows a preferred embodiment of the invention. A sampling pump 6 extracts a sample solution from the content in the conduit 1. This sample solution is divided into two parallel branches with approximately equal amounts in each branch. The first branch (to the right in FIG. 8) contains the urease-column 10 as well as the supply of carbon dioxide from a carbon dioxide source 41 via a dosage valve 60. The second branch contains a delay conduit or a delay vessel 22 which contains the same quantity of aluminium oxide as the urease-column 10 and additionally has the same flow resistance as the urease-column 10, but has no urease.

The contents of the urease-column 10 and the delay conduit 22 are supplied to heat exchanger coils 71, 72 of a heat exchanger 70, which contains a large amount of fluid. The content of each branch, 71 and 72, is transferred to each conductivity cell 7a and 7b, respectively. After the conductivity cells the two branches are combined to a single outlet conduit 73, in which a variable throttle device 53 is arranged and finally the sample solution is given off to a collection container 8 (or to conduit 1).

The inside of the heat exchanger is filled with a fluid which is kept at a very constant temperature. This fluid can be the dialysis fluid which passes in the conduit 1 or it can be another fluid which is heated to a desired constant temperature. In order to regulate the temperature there is a heating element 74 in an inlet 75 to the heat exchanger and a temperature sensor 76 in an outlet 77 from the heat exchanger. Additional temperature sensors can be placed in strategic positions in the heat exchanger 70. The heat exchanger is insulated from the surroundings to an extent which is suitable practically.

The conductivity cells 7a and 7b are connected to an electronic device 78 which provides the required voltages and measuring devices in order to carry out the conductivity measurement. The electronic device 78 further comprises a subtraction circuit in order to arrive at a difference between the measured values from the cells 7a and 7b as well as further possible arrangements for compensating the measured values for temperature. These functions are preferably carried out with the help of a microcomputer. The microcomputer also converts the measured values directly into the urea concentration in the sample solution.

The measured values may be corrected with respect to the prevailing temperature according to known techniques. The temperature of the solution in each sensor 7a and 7b is measured by temperature sensors 79 and 80. Since however the flow at the measurement points is very low, it is difficult to obtain reliable temperature measurements.

In order to obtain a sufficient accuracy in the determination of the urea concentration, it is necessary that the temperature difference between the solutions in the cells 7a and 7b is kept very small, in the order of magnitude of less than $\pm 0.01°$ C. We have found that if the tubes 71 and 72 are sufficiently long. and the temperature in the heat exchanger 70 is constant, sufficiently accurate measured values can be obtained.

In this case it is not necessary to temperature compensate each conductivity value before subtracting them, but the temperature compensation can be made on the differential conductivity. Then, a temperature value which is the mean value of the two solutions can be used.

As the mean value can be used the temperature of the heat exchanging fluid in the heat exchanger but outside the coils 71, 72. This temperature can be obtained by a temperature sensor, such as temperature sensor 110, shown in FIG. 9. The accuracy of the mean temperature need not be as high as mentioned above, but can be $\pm 0.4°$ C.

The fluid which is present within the heat exchanger 70 is preferably dialysis fluid from the conduit 1. In this way a relatively large flow can pass through the heat exchanger 70, which ensures that the temperature is substantially constant.

Alternatively a closed system can be used which is shown with dashed lines in FIG. 8, where a pump 81 circulates the fluid in an outer closed circuit 82.

The preferred embodiment according to FIG. 8 can be additionally complemented by a drainage device 25, 27 according to FIG. 1 in the left branch, which thereby contains a separate valve arrangement or pump.

In another alternative the arrangement according to FIG. 8 is provided with a cross-coupling which connects the urease column 10 with the tube 72 and the delay conduit 22 with the tube 71. In this way the measurement cells 7a and 7b respectively can be used alternately for the urease-column 10 and the delay conduit 22, whereby a reliable calibration can be obtained.

By using the throttle device 53 and the pump 6, an overpressure can be achieved in the urea-sensor in the order of magnitude of 0.1 MPa, whereby a sufficiently high solubility for the carbon dioxide is obtained before the urease column 10 for the intended linear measurement range up to 35 mM urea concentration. The reason for this linearity is above all that the conversion is based on reaction (5), which is heavily displaced to the right due to the catalysis by urease and the surplus of carbon dioxide as well as a low pH-value.

Figure 9:
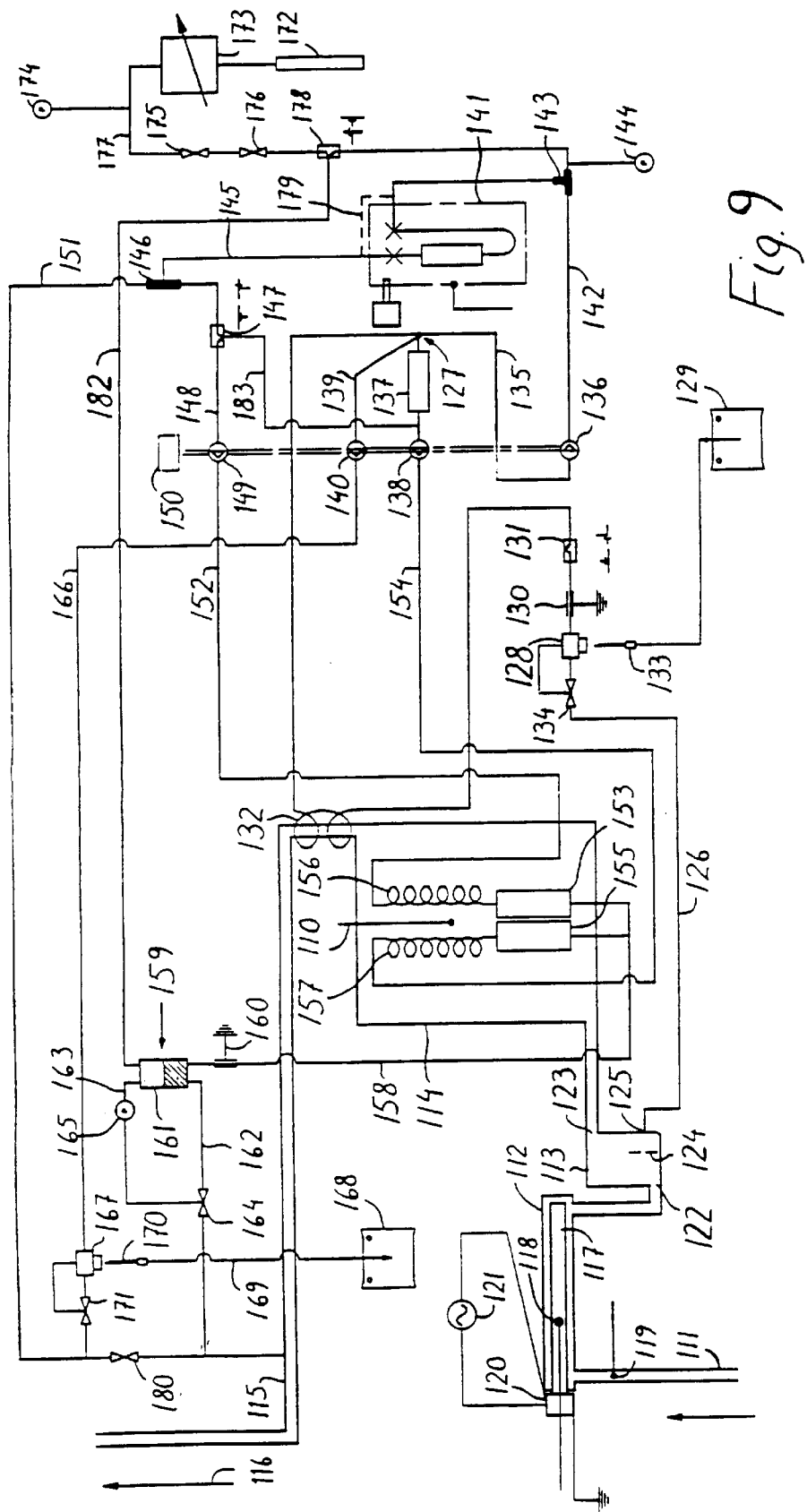
FIG. 9 is a detailed schematic representation of a preferred embodiment of the urea sensor according to the present invention.

FIG. 9 shows a more detailed flow scheme of the preferred embodiment of the urea sensor. The solution, enters from a dialysis machine via an inlet line 111 and enters a heater 112 and flows therefrom to a bubble separator 113. From there, the dialysate is conducted further on to a heat exchanger 114 and via an outlet line 115 to an outlet as shown by arrow 116.

The heater 112 comprises a heater rod 117 and a temperature sensor 118. Another temperature sensor 119 is positioned in the inlet line 111 immediately before the heater 112 and measures the temperature of the inlet dialysate. Moreover, there is a power measuring device 120 for measuring supplied power to the heater rod 117 via a suitable current source 121.

The inlet temperature of the dialysate in the line 111 is usually between about 20–37° C., for example about 34° C. The heater rod 117 is adapted to rise the temperature to for example about 42° C., which is sensed by a temperature sensor 110 positioned at heat exchanger 114.

By measuring the temperature difference between temperature sensor 110 and temperature sensor 119 and supplied power from the current source 121 by the power meter 120, the mass flow of dialysate through line 111 can be determined (a so-called thermal flow meter). Since the dialysate has an essentially constant composition, its specific heat capacitivity and density is approximately constant and the amount of dialysate., which is heated by the heater rod 117, can be determined as to its mass and/or volume.

Since the rise in temperature by means of the heater rod 117 is relatively slight, the accuracy of such a thermal flow meter will be low. The flow meter can be used for sensing that the inlet fluid flow via the inlet line 111 are within predetermined limits. Further possibilities of use appears from the description below.

The bubble separator 113 comprises a chamber having relatively large cross section so that :the flow velocity is low through the chamber from an inlet 122 at the lower end of the chamber to an outlet 123 at the upper end of the chamber. The bubble separator 113 is provided with a partition wall 124 and a second outlet 125 is adapted behind the partition wall 124 in relation to the inlet 122 in order to protect the outlet from turbulence. From outlet 125 a small partial quantity of the dialysate is taken out, a so-called sample solution of for example about 1% or less, which partial amount constitutes the fluid which is analyzed as to the contents of urea (or any other substance of interest). Thus, the sample solution taken out via outlet 25 will be comparatively free from gas bubbles.

The sample solution taken out passes from outlet 125 via a line 126 to a branch point 127. Line 126 comprises an inlet coupling 128 for a bag 129 enclosing a test solution, and a ground connection 130 for grounding the fluid in line 126. Moreover, there is an airation valve 131. Furthermore, line 126 may be winded a few revolutions around the dialysate line 115 as shown at 132 for equalizing possible temperature differences between the fluids in the lines.

Coupling 128 is intended for cooperation with a connector 133. When connector 133 is inserted in the coupling 128, a valve 134 in line 126 before coupling 128 is closed so that the contents of the bag 129 passes through line 126 to the branch point 127 instead of the sample solution.

The bag 129 including test solution may comprise about 50–100 ml test solution, which comprises urea in a known concentration. The test solution can be colder than the temperature of the dialysate of the sample solution, and that is why the heat exchanger 132 heats the sample solution to a certain degree. A volume of about 55 ml is sufficient for about 20 minutes use of the test solution.

At the branch point 127, the sample solution from line 126 is divided into three branches. The first branch goes via a line 135 to a pump 136 of peristaltic type. The second branch goes via a dummy volume 137 to a second pump 138 of peristaltic type. The third branch goes via a line 139 to a third pump 140 of peristaltic type.

From pump 136, the sample solution passes further on via a line 142 to a urease column 141 in the nature of a disposable article. The column comprises a sufficient amount of urease and further material required for transforming the urea contents of the sample solution to ammonium ions and bicarbonate ions as described above. The column 141 is shaped as a cartridge having a specific shape and with connections so that it easily be connected to the urea sensor.

Before the urease column 141 there is supplied carbon dioxide gas to the line 142, for example in a T-coupling 143. The pressure of the supplied gas is measured by a pressure meter 144. The amount of gas supplied is controlled by a valve arrangement as closer described below.

In the urease column 141, the urea contents of the solution is decomposed into ammonium ions and bicarbonate ions. The transformed solution is passed via a line 145 to a bubble separator 146. From the outlet connection of the bubble separator, the solution passes further on via a valve 147 (closer described below) via a line 148 to a fourth pump 149.

All pumps 136, 138, 140, 149 are driven by a common motor 150 via a common shaft or via any suitable transmission. The pumps are preferably so-called peristaltic pumps. The pump 136 has preferably a slightly larger capacity than the other pumps, which mutually have the same capacity, which can be about 0.6 ml/min for the pumps 138, 140, 149 and about 20% more for the pump 136. The pump 140 can have a different and/or separate capacity.

During normal operation, a closed system prevails between the first pump 136, line 142, urease column 141, line 145, bubble separator 146, via valve 147, line 148 and pump 139. Thus, the difference in capacity (about 20%) between pumps 136 and 149 must be given off via the second line 151 of the bubble separator for separated gases. Thus, the inlet solution via line 145 to the bubble separator 146 is divided in two flows, 20% via line 151 and 80% via line 148. The major portion of the gas contents of the inlet line 145 passes out via the upper outlet to line 151.

The solution which passes out through line 148 to pump 149 is thus more or less completely free from gases. This solution is conducted further on via a line 152 to a conductivity measurement cell 153 (below named condcell).

From the branch point 127 a partial amount of the sample solution is passed via the volume 137 and the pump 138 and via a line 154 to a second condcell 155. In this way there is obtained a time delay of said partial amount passing the volume 137, which is approximately equally large as the time delay for the partial amount which passes the urease column.

Before the solutions in the lines 152 and 154 reaches each respective condcell 153, 155, the solution passes through tubes, for example in the shape of heat exchanger coils 156, 157 positioned in the heat exchanger 114 and thus surrounded by dialysis solution of relatively constant temperature. The conditions are such that the solutions in the two coils 156, 157 have passed through approximately the same volumes and lengthes of lines at their way to the coils 156, 157. Moreover, the coils are positioned very tight adjacent to each other in the heat exchanger, which means that the temperature of the two solutions are equal or very similar, typically less than a difference of 0.01° C.

The difference in conductivity between the two solutions depends on the contents of ammonium ions and bicarbonate ions in the catalytically decomposed solution, which thus can be measured and correlated to the urea contents.

Due to the supply of carbon dioxide, the relationship between the amount of urea and ammonium ions is linear over a large area sufficient for the measurement of the present invention. Thus, no calibrations are required for corrections for possible deviations from a linear relationship.

From the two condcells 153, 155, the solution passes further on via a common line 158 to a pressure equalizing device 159. In line 158 there is further placed a ground connection 160 in order to ensure that no electric disturbances enter via the solution from the surroundings.

The pressure equalization device 159 comprises a container 161 having an inlet connection from line 158 and an outlet connection to an outlet line 162 both preferably in the bottom 161. In the upper end of the container there is a connection to a line 163, which terminates with a pressure meter 165. The signal from the pressure meter 165 controls the opening degree of a valve 164 positioned in outlet line 162.

When solution enters the container 161 via line 158, the container is filled and air passes out via line 163 and influences upon the pressure meter 165. When a certain predetermined pressure prevails in the container 161, valve 164 is opened and allows the solution to pass out via line 162 and valve 164. Thus, a certain predetermined pressure is maintained in container 161 and controlled via the remaining amount of air in container 161 and the valve 164.

The remaining amount of air in container 164 operates as an air cushion which damps possible pressure oscillations which may have a tendence of occuring during for example a pump stroke. By means of device 159, an overpressure is obtained in the lines between the pumps and up to device 159. This overpressure means that possible remaining carbon dioxide in the solution which passes via line 152 and other possible remaining gas bubbles in the solutions reaching the condcells will dissolve in the liquid. In this way problems in connection with the measuring in the condcells are avoided. It is known that gas bubbles considerably disturb the measurement in the condcells.

It is also possible to change the pressure of device 159 by closing valve 164 so that the pressure increases temporary or intermittent. A change of the conductivity value (especially an increase) at increased pressure indicates error in the condcells, as described above.

The present invention uses double gas separators, a first separator 122 for taking out a sample from the dialysis solution which is essentially free from bubbles, and a second separator 146, which separates a possible excess of supplied carbon dioxide gas. Moreover, the extra safety measure of an increased pressure is used. The solubility of gas in a liquid decreases with increased temperature, but the temperature is relatively constant in the present invention.

From valve 164, the solution passes out to the outlet line 115 for dialysate solution and is delivered to a waste etc.

The third pump 140 is connected to the branch point 127 via line 139 and takes out a test sample with constant flow speed, for example about 0,6 ml/min. From pump 140 this sample solution passes via a line 166 to an outlet 167 and via a valve 171 to the outlet line 115. In the outlet 167 can be inserted a connector 170 which via a line 169 is connected to a collection bag 168. When the connector 170 is inserted in the outlet 167, valve 171 is closed and all the solution in line 166 must pass to the collection vessel 168.

Preferably pump 150 is driven with constant speed in order to take out a constant partial amount of the dialysate solution passing through the entire urea sensor. Alternatively, pump 150 can be driven with a speed which is proportional to the amount of dialysate solution passing in outlet line 115, for example with a proportion constant of 1:500 and is used for the purpose stated in European patent application 94.102383.0. In this case, motor 150 which drives pumps 136, 138, 140, 149 is controlled by a signal obtained from the dialysis machine so that said proportionality constant is obtained. Alternatively, it is possible to use the measurement of the dialysis flow achieved via the heater rod 117 and corresponding temperature sensors 110, 119.

Carbon dioxide gas is supplied via the T-connection 143 to the sample solution as described above. The carbon dioxide gas is obtained from a suitable source 132 for carbon dioxide gas, which can be a carbon dioxide cartridge or a device for generating carbon dioxide gas in situ.

The pressure from the source of carbon dioxide gas is controlled with a regulator 173 of known construction and the outlet pressure is monitored by a pressure sensor.

Two valves 175, 176 are adapted in a line 177 leading from the pressure regulator 173 to said T-coupling 143. Valves 175, 176 are controlled so that when one is open the other is closed. By controlling the frequency for opening and closing of said valves, the amount of carbon dioxide gas passing valves 175, 176 is controlled if the pressure difference across the valves is known. The pressure difference is measured by the pressure sensors 174 and 144.

The amount of carbon dioxide gas introduced in the branch point 143 is controlled so that a sufficient amount of carbon dioxide gas is introduced while a too large excess is avoided.

Line 177 comprises a valve 178 connecting line 177 with container 159 under certain operation conditions such as disinfection of the system.

There is a bypass-line 179 bypassing the urease column 141 when it is taken out from its holder.

Heat exchanger 114 comprises a cylindrical or rectangular container 180 having a relatively large volume, for example 2 dl. The dialysate surrounds the heat coils 156 and 157 so that they obtain the same temperature as the dialysate and mutually the same temperature to a very large accuracy.

Figure 10:
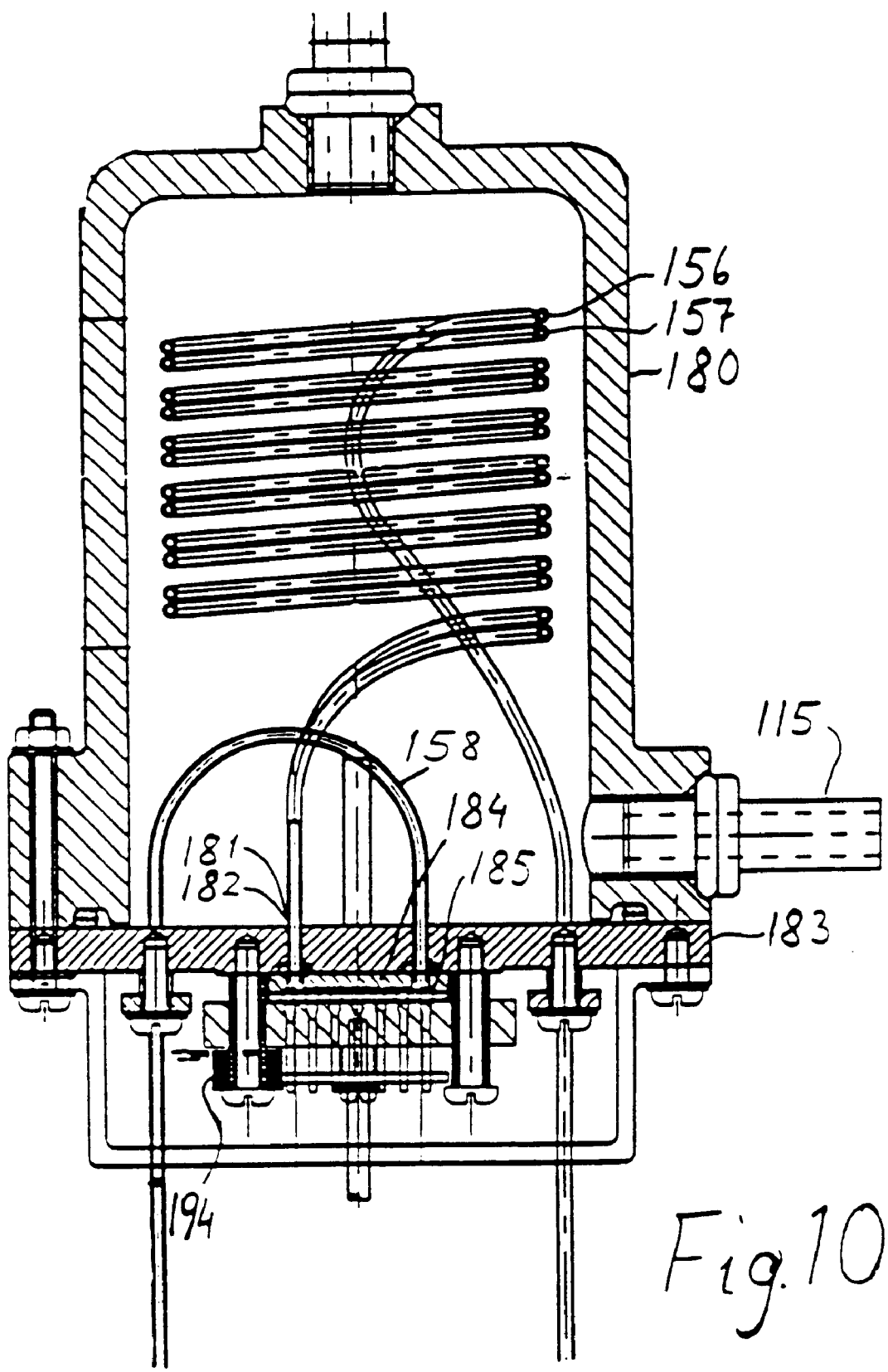
FIG. 10 is an elevational, cross-sectional view through the heat exchanger included in the urea sensor according to FIG. 9.

The condcells 153, 155 are positioned in the bottom of the container at the outside of the container 180 as more closely appears from FIG. 10. The heat coils 156, 157 terminate in two openings 181 and 182 through the relatively thick bottom 183 of the container. At the outside of the bottom 183 (or in a recess in the bottom plate), the two condcells 153, 155 are integrated to a single unit on the same substrate. Thus, it is assured that they adopt the same temperature. By having both cells in close thermal prixmity, the accuracy required for the temperature sensor is reduced.

Figure 11:
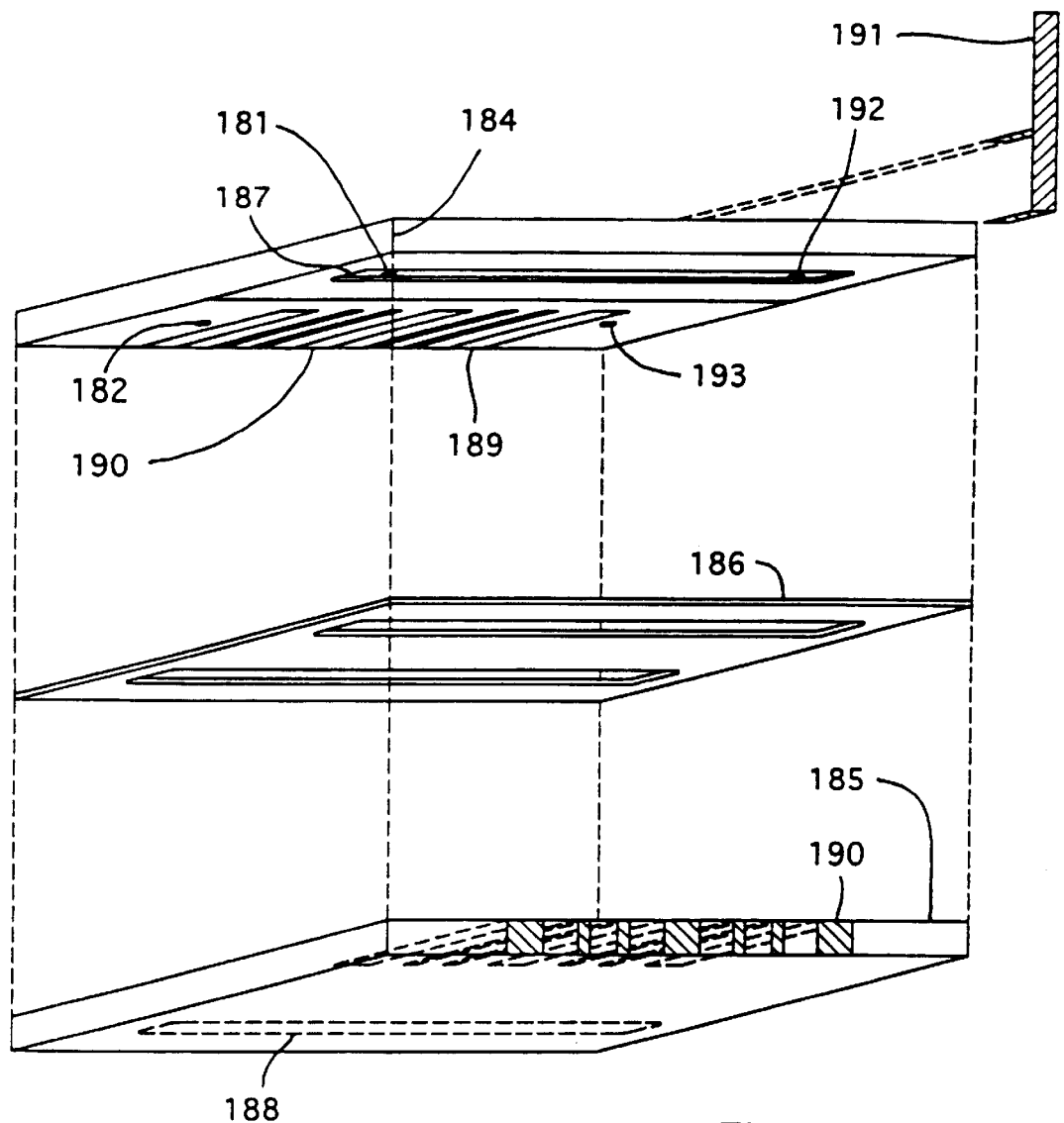
FIG. 11 is a perspective exploded view of a double conductivity cell positioned at the bottom of the heat exchanger according to FIG. 10.

As shown in FIG. 11, the condcells comprise two plates 184, 185, which are made for example of sapphir and comprise each a longitudinal concave recess 187, 188, respectively. The plates are entirely symmetrical and are faced against each other and connected against each other with spring loaded attachment means (not shown in FIG. 11) so that a sealing 186 between the sapphir plates is always loaded. The sealing 186 can be made very thin and is made of a plastic material, which is inert in relation to the dialysate, such as polypropylene.

Opposite the corresponding recess 187, 188 there are several gold electrodes 189, 190, which extend out to the sides of the plate. Each electrode cooperates with a corresponding contact 191, only one of which is shown in FIG. 11. There are in principal six equal electrodes 189, positioned symmetrically around a common electrode 190.

Between the two outer electrodes 189 and the electrode 190 there is applied an electric current via a current generator. The voltage over the two next following electrodes on each side is measured and gives two measurement signals which in principal should be equally large (possibly after correction due to different distances).

The gold electrodes 189, 190 can be applied by means of known techniques, such as plating or by means of ion assists or ion implant. Other known methods can also be used.

Since the plates are made of sapphire having a good thermal conductivity, only small temperature differences occur internally in the condcell. Of course, also other conventional materials can be used.

The sample solution enters through holes 181, 182, respectively, to each recess 187, 188 and passes in the same direction to outlet holes 192, 193 in order to obtain similar temperature conditions. It is alternatively possible that the flow through the recesses takes place in opposite directions.

In an alternative embodiment, each plate has two recesses and the plates are so positioned that each recess faces a corresponding recess in the other plate. A further alternative is to provide one plate with two recesses while the other plate is plain and provided with the electrodes.

In all other respects, the operation is identical to the embodiment described above.

The plates 184, 185 are maintained against each other by means of spring loaded attachment means 194 as shown in FIG. 10. There can be many such attachment means distributed over the periphery of the plates in order to give a uniform pressure distribution on the plates 184, 185 and the sealing 86 interposed therebetween. Also the contacts 191 contribute to keeping the plates together.

The urea sensor described above requires cleaning and disinfection with regular intervalls in order to maintain a high accuracy. Disinfection with heat can be performed at the same time as the dialysis machine which the urea sensor is connected to. Disinfection can take place after each treatment or each day.

When the dialysis machine is disinfected, dialysate having increased temperature passes through the urea sensor, which is sensed by the temperature sensors 119 and 110. Then, the operation of the urea sensor is also switched over to heat disinfection and the heater rod 117 heats the inlet dialysate further to a temperature of about 95° C. The urease column 141 has to be disconnected and the bypass line 179 is activated since the urease material does not withstand high temperatures. In this way an effective heat disinfection of the urea sensor is obtained. The urea sensor can also be cleaned by chemical means.

Figure 12:
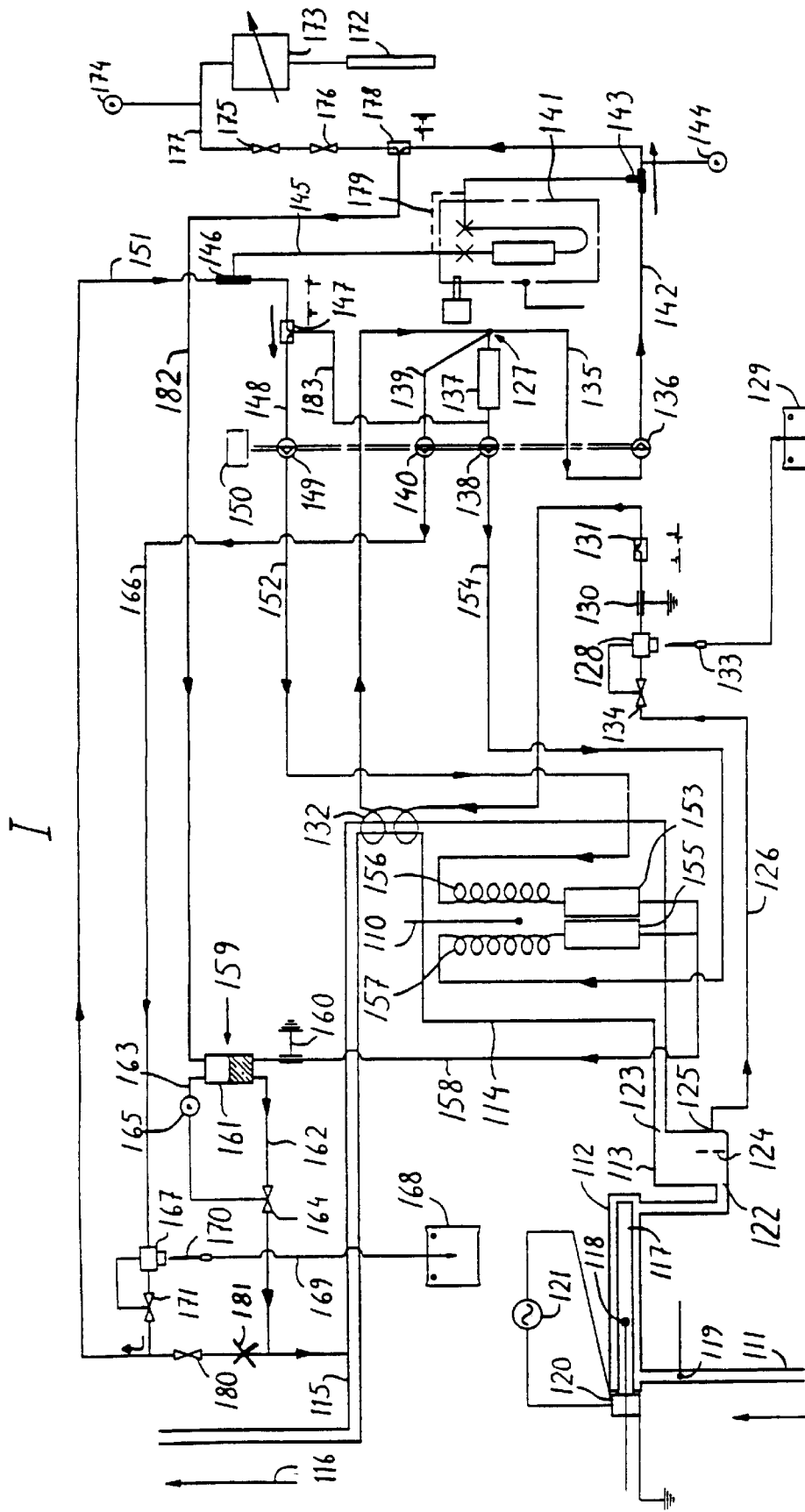
FIG. 12 is a schematic representation of a device similar to the device shown in FIG. 9, showing the urea sensor during disinfection.
Figure 13:
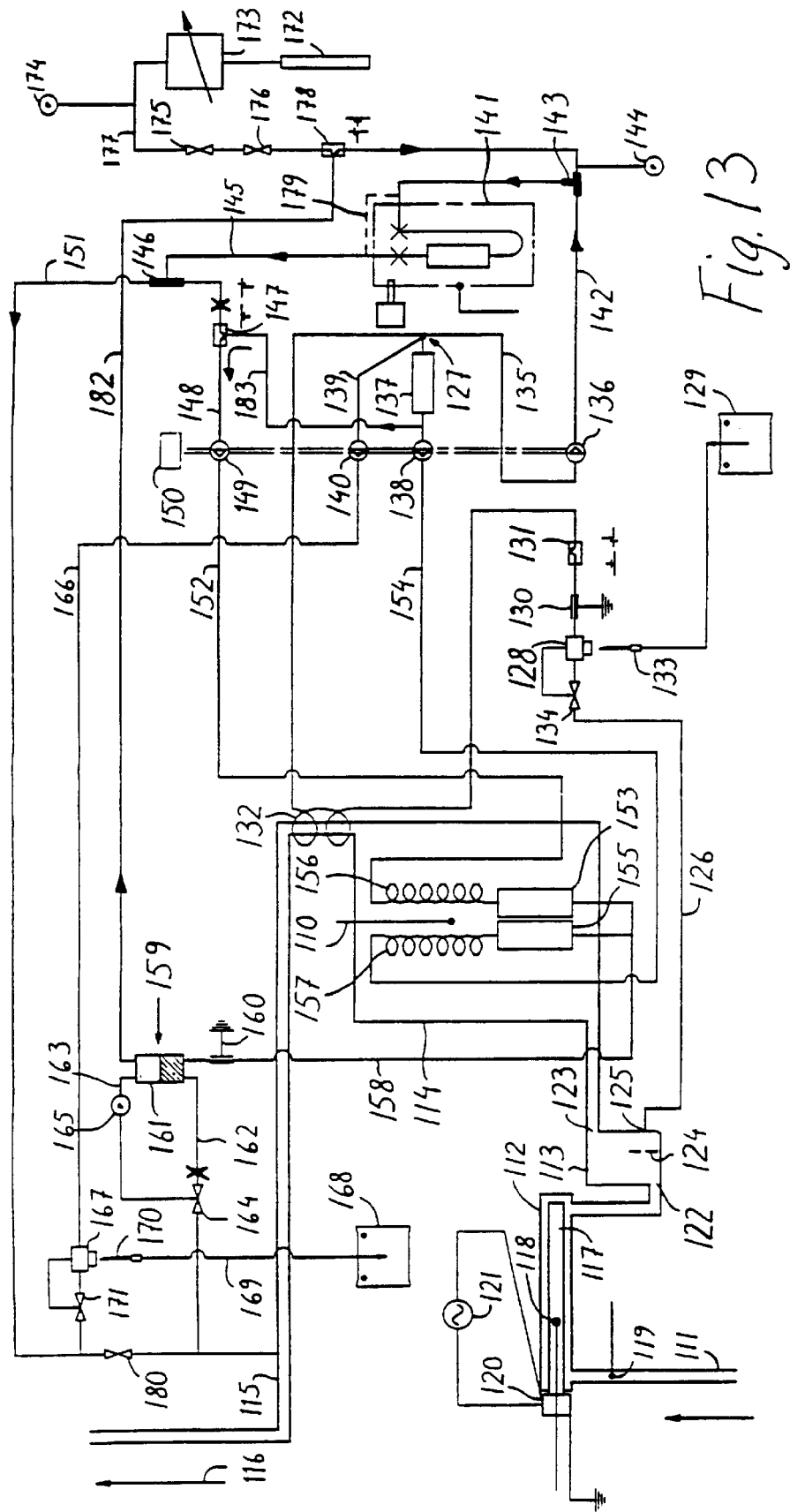
FIG. 13 is a schematic representation of a device similar to the device shown in FIG. 9, showing the urea sensor during disinfection.

At disinfection (chemical and/or with heat) the valves are placed in certain positions as shown in FIG. 12 and FIG. 13.

FIG. 12 shows disinfection, phase one. Then, fluid passes from inlet 125 via line 126, valve 131, coil 132 to point 127. From point 127, the fluid passes further on via pump 138, line 154, coil 157, cell 155, line 158, vessel 161 and valve 164 to the outlet 116. Moreover, the solution passes from point 127 via line 139, pump 140, line 166, connector 167 to valve 171.

Valve 180, which connects valve 171 to the outlet is, however, closed as is shown by the cross 181 in FIG. 12. Thus, the solution in line 166 must pass via valve 171 and backwards in line 151 to the bubble separator 146 and then via valve 147, line 148, pump 149, line 152, coil 156, cell 153 to the line 158 and further on to the outlet.

At the same time the solution passes from point 127 via line 135 and pump 136 to the line 142. Due to the flow conditions, the pressure at point 143 and the pressure at the inlet to the bubble chamber 146 are approximately equal and that is why the solution does not pass through the bypass line 179 via line 145 to the bubble separator 146 but instead passes from the branch point 143 and backwards in line 177 (where it is normally only carbon dioxide) and then via valve 178 and line 182 to the upper end of the chamber 159. In this first phase the main part of the system is disinfected except for valve 180 and line 145 and bypass line 179.

In the second phase of the cleaning as shown in FIG. 13, valve 180 is switched over so that it is open and valve 147 is switched for connecting line 148 with a line 183 and to block the connection between the bubble separator 146 and the line 148. By this measure, the line 145 and the bypass line 179 are disinfected with a large flow, which gives a high heating (at heat disinfection). Moreover, valve 164 is closed which means that the flow in line 182 changes direction and goes from chamber 159 to valve 178 and the point 143.

The present invention has above been described with reference to several embodiments shown on the drawings. The invention can however be varied and modified in many manners within the scope of the invention. The different single features shown in one or the other drawings can be combined in manners different from those shown on the drawings. Such modifications, which are obvious to a skilled person reading this specification, is intended to be within the scope of the invention. The invention is only limited by the appended patent claims.

What is claimed is:

1. Apparatus for measuring the concentration of a decomposable compound in a solution comprising charging means for charging a buffer in gaseous form to said solution, a reactor for decomposing said decomposable compound whereby a reacted solution is formed, and measuring means for measuring the conductivities of said solution and said reacted solution whereby a differential conductivity can be calculated therefrom.

2. The apparatus of claim 1 wherein said buffer in gaseous form comprises carbon dioxide.

3. The apparatus of claim 2 wherein said decomposable compound comprises urea.

4. The apparatus of claim 3 wherein said solution comprises bicarbonate ions.

5. The apparatus of claim 2 wherein said decomposing of said decomposable compound comprises catalytically reacting said solution.

6. The apparatus of claim 5 wherein said catalytic reacting comprises reacting said solution with urease.

7. The apparatus of claim 2 including a silicon tube in contact with said solution whereby said carbon dioxide can be added to said solution by diffusion through said silicon tube.

8. The apparatus of claim 1 including a bubble detector for detecting bubbles in said reacted solution.

9. The apparatus of claim 2 including pressure increasing means for increasing the pressure of said solution in order to increase the solubility of said carbon dioxide in said solution.

10. The apparatus of claim 9 wherein said pressure increasing means is adapted to create a pressure of about 0.1 MPa.

11. The apparatus of claim 2 including temperature decreasing means for decreasing the temperature of said solution in order to increase the solubility of said carbon dioxide in said solution during said measuring step.

12. The apparatus of claim 11 wherein said temperature decreasing means is adapted to decrease said temperature to about 25° C.

13. The apparatus of claim 1 wherein said measuring means for measuring the conductivity of said solution and said reacted solution comprises a single measurement cell.

14. The apparatus of claim 1 comprising a first conduit path and a second conduit path, said first conduit path including said reactor, and wherein said measuring means for measuring the conductivities of said solution and said reacted solution comprises a first measuring means for measuring the conductivity of said solution and a second measuring means for measuring the conductivity of said reacted solution, said first measuring means being located in said second conduit path and said second measuring means being located in said first conduit path.

15. The apparatus of claim 14 wherein said second conduit path is configured so that the flow of said solution through said first and second conduit paths to said first and second measurement cells takes approximately the same amount of time.

16. The apparatus of claim 14 wherein said heat exchanger is disposed for maintaining the temperature of said solutions in said first and second conduit paths approximately equal.

17. The apparatus of claim 4 wherein said reacted solution has a pH of between about 6 and 8.

18. The apparatus of claim 17 wherein said reacted solution has a pH of between about 6 and 7.4.

19. The apparatus of claim 4 wherein said catalyzed reaction in said reactor comprises the following reaction:

$$(NH_2)_2CO + CO_2 + 3H_2O \rightarrow 2NH_4^+ + 2HCO_3^-.$$

* * * * *